United States Patent
Hudson et al.

(10) Patent No.: US 10,308,931 B2
(45) Date of Patent: Jun. 4, 2019

(54) METHODS FOR SCREENING PROTEINS USING DNA ENCODED CHEMICAL LIBRARIES AS TEMPLATES FOR ENZYME CATALYSIS

(71) Applicant: Gen9, Inc., Cambridge, MA (US)

(72) Inventors: Michael E. Hudson, Framingham, MA (US); Joseph Jacobson, Newton, MA (US)

(73) Assignee: Gen9, Inc., Boston, MA (US)

( * ) Notice: Subject to any disclaimer, the term of this patent is extended or adjusted under 35 U.S.C. 154(b) by 136 days.

(21) Appl. No.: 14/840,551

(22) Filed: Aug. 31, 2015

(65) Prior Publication Data

US 2015/0361420 A1   Dec. 17, 2015

Related U.S. Application Data

(62) Division of application No. 13/799,039, filed on Mar. 13, 2013, now Pat. No. 9,150,853.

(60) Provisional application No. 61/613,845, filed on Mar. 21, 2012, provisional application No. 61/614,213, filed on Mar. 22, 2012.

(51) Int. Cl.
  *C12N 15/10*   (2006.01)

(52) U.S. Cl.
  CPC ..... *C12N 15/1034* (2013.01); *C12N 15/1037* (2013.01); *C12N 15/1086* (2013.01)

(58) Field of Classification Search
  CPC ............ C12N 15/1034; C12N 15/1037; C12N 15/1086
  USPC ........................................................ 506/11
  See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis et al. |
| 4,683,202 A | 7/1987 | Mullis |
| 4,689,405 A | 8/1987 | Frank et al. |
| 4,725,677 A | 2/1988 | Koester et al. |
| 4,800,159 A | 1/1989 | Mullis et al. |
| 4,888,286 A | 12/1989 | Crea |
| 4,959,317 A | 9/1990 | Sauer |
| 4,965,188 A | 10/1990 | Mullis et al. |
| 4,999,294 A | 3/1991 | Looney et al. |
| 5,047,524 A | 9/1991 | Andrus et al. |
| 5,093,251 A | 3/1992 | Richards et al. |
| 5,096,825 A | 3/1992 | Barr et al. |
| 5,104,789 A | 4/1992 | Permar et al. |
| 5,104,792 A | 4/1992 | Silver et al. |
| 5,132,215 A | 7/1992 | Jayaraman et al. |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,395,750 A | 3/1995 | Dillon et al. |
| 5,405,783 A | 4/1995 | Pirrung et al. |
| 5,424,186 A | 6/1995 | Fodor et al. |
| 5,436,150 A | 7/1995 | Chandrasegaran |
| 5,436,327 A | 7/1995 | Southern et al. |
| 5,445,934 A | 8/1995 | Fodor et al. |
| 5,459,039 A | 10/1995 | Modrich et al. |
| 5,474,796 A | 12/1995 | Brennan |
| 5,498,531 A | 3/1996 | Jarrell |
| 5,508,169 A | 4/1996 | Deugau et al. |
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor et al. |
| 5,556,750 A | 9/1996 | Modrich et al. |
| 5,604,097 A | 2/1997 | Brenner |
| 5,605,793 A | 2/1997 | Stemmer |
| 5,624,711 A | 4/1997 | Sundberg et al. |
| 5,639,603 A | 6/1997 | Dower et al. |
| 5,641,658 A | 6/1997 | Adams et al. |
| 5,653,939 A | 8/1997 | Hollis et al. |
| 5,674,742 A | 10/1997 | Northrup et al. |
| 5,679,522 A | 10/1997 | Modrich et al. |

(Continued)

FOREIGN PATENT DOCUMENTS

| | | |
|---|---|---|
| CN | 1145641 | 3/1997 |
| CN | 1468313 | 1/2004 |

(Continued)

OTHER PUBLICATIONS

Lederman et al., "DNA-directed peptide synthesis I. A comparison of T2 and *Escherichia coli* DNA-Directed Peptide Synthesis in Two Cell-Free Systems", Biochim, Biophys. Acta, vol. 149, pp. 235-258, (1967).
Smith et al., "Single-step purification of polypeptides expressed in *Escherichia coli* as fusions with glutathione S-transferase", Gene, vol. 67, Issue 1, pp. 31-40, (1988).
Demeler et al., "Neural network optimization for *E. coli* promoter prediction," Nucl. Acids. Res. 19:1593-1599 (1991).
Roberts and Szostak, "RNA-peptide fusions for the in vitro selection of peptides and proteins," Proc Natl Acad Sci USA. 94(23): 12297-302.
TnT® coupled reticulocyte lysate system, Technical Bulletin (Promega, Madison, Wis), 2013.

(Continued)

*Primary Examiner* — Karla A Dines
(74) *Attorney, Agent, or Firm* — Choate, Hall & Stewart LLP; Brenda Herschbach Jarrell; Robert N. Sahr

(57) ABSTRACT

Disclosed are methods, compositions and devices for screening a protein library for proteins having a desired activity, such as capable of catalyzing the formation of a bond between two reactants. In an exemplary embodiments, a plurality of proteins are expressed in vitro from a plurality of nucleic acids, the plurality of proteins are exposed with two single stranded oligonucleotides having complementary sequences, each oligonucleotide having a reactant and a fluorophore, the fluorescence of the protein-reactant-oligonucleotide-fluorophore complexes is detected and the complexes showing detectable fluorescence energy transfer are isolated, thereby isolating proteins having the desired enzymatic activity.

5 Claims, 7 Drawing Sheets

Specification includes a Sequence Listing.

(56) References Cited

U.S. PATENT DOCUMENTS

| | | |
|---|---|---|
| 5,695,940 A | 12/1997 | Drmanac et al. |
| 5,700,637 A | 12/1997 | Southern |
| 5,700,642 A | 12/1997 | Monforte et al. |
| 5,702,894 A | 12/1997 | Modrich et al. |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor et al. |
| 5,830,655 A | 11/1998 | Monforte et al. |
| 5,830,721 A | 11/1998 | Stemmer et al. |
| 5,834,252 A | 11/1998 | Stemmer et al. |
| 5,858,754 A | 1/1999 | Modrich et al. |
| 5,861,482 A | 1/1999 | Modrich et al. |
| 5,871,902 A | 2/1999 | Weininger et al. |
| 5,877,280 A | 3/1999 | Wetmur |
| 5,912,129 A | 6/1999 | Vinayagamoorthy et al. |
| 5,916,794 A | 6/1999 | Chandrasegaran |
| 5,922,539 A | 7/1999 | Modrich et al. |
| 5,928,905 A | 7/1999 | Stemmer et al. |
| 5,929,208 A | 7/1999 | Heller et al. |
| 5,942,609 A | 8/1999 | Hunkapiller et al. |
| 5,953,469 A | 9/1999 | Zhou |
| 6,008,031 A | 12/1999 | Modrich et al. |
| 6,013,440 A | 1/2000 | Lipshutz et al. |
| 6,017,696 A | 1/2000 | Heller |
| 6,027,877 A | 2/2000 | Wagner, Jr. |
| 6,042,211 A | 3/2000 | Hudson et al. |
| 6,093,302 A | 7/2000 | Montgomery |
| 6,103,463 A | 8/2000 | Chetverin et al. |
| 6,110,668 A | 8/2000 | Strizhov et al. |
| 6,136,568 A | 10/2000 | Hiatt et al. |
| 6,143,527 A | 11/2000 | Pachuk et al. |
| 6,150,102 A | 11/2000 | Mills, Jr. et al. |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson et al. |
| 6,248,521 B1 | 6/2001 | Van Ness et al. |
| 6,261,797 B1 | 7/2001 | Sorge et al. |
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer |
| 6,315,958 B1 | 11/2001 | Singh-Gasson et al. |
| 6,322,971 B1 | 11/2001 | Chetverin et al. |
| 6,326,489 B1 | 12/2001 | Church et al. |
| 6,333,153 B1 | 12/2001 | Fishel et al. |
| 6,346,399 B1 | 2/2002 | Weissman et al. |
| 6,355,412 B1 | 3/2002 | Stewart et al. |
| 6,355,423 B1 | 3/2002 | Rothberg et al. |
| 6,358,712 B1 | 3/2002 | Jarrell et al. |
| 6,365,355 B1 | 4/2002 | McCutchen-Maloney |
| 6,372,429 B1 | 4/2002 | Sharon |
| 6,372,434 B1 | 4/2002 | Weissman |
| 6,372,484 B1 | 4/2002 | Ronchi et al. |
| 6,375,903 B1 | 4/2002 | Cerrina et al. |
| 6,376,246 B1 | 4/2002 | Crameri et al. |
| 6,406,847 B1 | 6/2002 | Cox et al. |
| 6,410,220 B1 | 6/2002 | Hodgson |
| 6,416,164 B1 | 7/2002 | Stearns et al. |
| 6,426,184 B1 | 7/2002 | Gao et al. |
| 6,432,360 B1 | 8/2002 | Church |
| 6,444,111 B1 | 9/2002 | Montgomery |
| 6,444,175 B1 | 9/2002 | Singh-Gasson et al. |
| 6,444,650 B1 | 9/2002 | Cech et al. |
| 6,444,661 B1 | 9/2002 | Barton et al. |
| 6,472,184 B1 | 10/2002 | Hegemann et al. |
| 6,479,652 B1 | 11/2002 | Crameri et al. |
| 6,480,324 B2 | 11/2002 | Quate et al. |
| 6,489,146 B2 | 12/2002 | Stemmer |
| 6,495,318 B2 | 12/2002 | Harney |
| 6,506,603 B1 | 1/2003 | Stemmer |
| 6,509,156 B1 | 1/2003 | Stewart |
| 6,511,849 B1 | 1/2003 | Wang |
| 6,514,704 B2 | 2/2003 | Bruce et al. |
| 6,521,427 B1 | 2/2003 | Evans |
| 6,534,271 B2 | 3/2003 | Furste |
| 6,537,776 B1 | 3/2003 | Short |
| 6,565,727 B1 | 5/2003 | Shenderov |
| 6,586,211 B1 | 7/2003 | Stahler et al. |
| 6,593,111 B2 | 7/2003 | Baric et al. |
| 6,596,239 B2 | 7/2003 | Williams et al. |
| 6,605,451 B1 | 8/2003 | Marmaro et al. |
| 6,610,499 B1 | 8/2003 | Fulwyler et al. |
| 6,613,581 B1 | 9/2003 | Wada et al. |
| 6,632,641 B1 | 10/2003 | Brennan |
| 6,650,822 B1 | 11/2003 | Zhou |
| 6,658,802 B2 | 12/2003 | Lucas, Jr. et al. |
| 6,660,475 B2 | 12/2003 | Jack et al. |
| 6,664,112 B2 | 12/2003 | Mulligan et al. |
| 6,664,388 B2 | 12/2003 | Nelson |
| 6,670,127 B2 | 12/2003 | Evans |
| 6,670,605 B1 | 12/2003 | Storm, Jr. et al. |
| 6,800,439 B1 | 10/2004 | McGall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | McGall et al. |
| 6,846,655 B1 | 1/2005 | Wagner et al. |
| 6,897,025 B2 | 5/2005 | Cox et al. |
| 6,911,132 B2 | 6/2005 | Pamula et al. |
| 6,921,818 B2 | 7/2005 | Sproat |
| 6,932,097 B2 | 8/2005 | Ellson et al. |
| 6,946,296 B2 | 9/2005 | Patten et al. |
| 6,955,901 B2 | 10/2005 | Schouten |
| 6,969,587 B2 | 11/2005 | Taylor |
| 6,969,847 B2 | 11/2005 | Davis et al. |
| 7,090,333 B2 | 8/2006 | Mutz et al. |
| 7,133,782 B2 | 11/2006 | Odedra |
| 7,144,734 B2 | 12/2006 | Court et al. |
| 7,169,560 B2 | 1/2007 | Lapidus et al. |
| 7,179,423 B2 | 2/2007 | Bohm et al. |
| 7,183,406 B2 | 2/2007 | Belshaw |
| 7,199,233 B1 | 4/2007 | Jensen et al. |
| 7,262,031 B2 | 8/2007 | Lathrop |
| 7,273,730 B2 | 9/2007 | Du Breuil Lastrucci |
| 7,285,835 B2 | 10/2007 | Rizzo et al. |
| 7,303,320 B1 | 12/2007 | Ashley |
| 7,303,872 B2 | 12/2007 | Sussman |
| 7,323,320 B2 | 1/2008 | Oleinikov |
| 7,399,590 B2 | 7/2008 | Piepenburg et al. |
| 7,432,055 B2 | 10/2008 | Pemov et al. |
| 7,498,176 B2 | 3/2009 | McCormick et al. |
| 7,537,897 B2 | 5/2009 | Brenner et al. |
| 7,563,600 B2 | 7/2009 | Oleinikov |
| 7,699,979 B2 | 4/2010 | Li et al. |
| 7,723,077 B2 | 5/2010 | Young et al. |
| 7,820,412 B2 | 10/2010 | Belshaw et al. |
| 7,879,580 B2 | 2/2011 | Can et al. |
| 7,932,025 B2 | 4/2011 | Can et al. |
| 8,053,191 B2 | 11/2011 | Blake |
| 8,058,004 B2 | 11/2011 | Oleinikov |
| 8,137,906 B2 | 3/2012 | Schatz |
| 8,173,368 B2 | 5/2012 | Staehler et al. |
| 8,476,018 B2 | 7/2013 | Brenner |
| 8,716,467 B2 | 5/2014 | Jacobson |
| 8,808,986 B2 | 8/2014 | Jacobson et al. |
| 9,023,601 B2 | 5/2015 | Oleinikov |
| 9,023,649 B2 | 5/2015 | Mali et al. |
| 9,051,666 B2 | 6/2015 | Oleinikov |
| 9,150,853 B2 | 10/2015 | Hudson et al. |
| 9,295,965 B2 | 3/2016 | Jacobson et al. |
| 9,322,037 B2 | 4/2016 | Liu et al. |
| 9,752,176 B2 | 9/2017 | Kung et al. |
| 2001/0012537 A1 | 8/2001 | Anderson et al. |
| 2001/0031483 A1 | 10/2001 | Sorge et al. |
| 2001/0049125 A1 | 12/2001 | Stemmer et al. |
| 2001/0053519 A1 | 12/2001 | Fodor et al. |

(56) References Cited

U.S. PATENT DOCUMENTS

| | | |
|---|---|---|
| 2002/0012616 A1 | 1/2002 | Zhou et al. |
| 2002/0025561 A1 | 2/2002 | Hodgson |
| 2002/0037579 A1 | 3/2002 | Ellson et al. |
| 2002/0058275 A1 | 5/2002 | Fishel et al. |
| 2002/0081582 A1 | 6/2002 | Gao et al. |
| 2002/0127552 A1 | 9/2002 | Church et al. |
| 2002/0132259 A1 | 9/2002 | Wagner et al. |
| 2002/0132308 A1 | 9/2002 | Liu et al. |
| 2002/0133359 A1 | 9/2002 | Brown |
| 2003/0017552 A1 | 1/2003 | Jarrell et al. |
| 2003/0044980 A1 | 3/2003 | Mancebo et al. |
| 2003/0047688 A1 | 3/2003 | Faris et al. |
| 2003/0050437 A1 | 3/2003 | Montgomery |
| 2003/0050438 A1 | 3/2003 | Montgomery |
| 2003/0054390 A1 | 3/2003 | Crameri et al. |
| 2003/0068633 A1 | 4/2003 | Belshaw et al. |
| 2003/0068643 A1 | 4/2003 | Brennan et al. |
| 2003/0082630 A1 | 5/2003 | Kolkman et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0143550 A1 | 7/2003 | Green et al. |
| 2003/0143724 A1 | 7/2003 | Cerrina et al. |
| 2003/0165841 A1 | 9/2003 | Burgin et al. |
| 2003/0170616 A1 | 9/2003 | Wang et al. |
| 2003/0171325 A1 | 9/2003 | Gascoyne et al. |
| 2003/0175907 A1 | 9/2003 | Frazer et al. |
| 2003/0186226 A1 | 10/2003 | Brennan et al. |
| 2003/0198948 A1 | 10/2003 | Stahler et al. |
| 2003/0215837 A1 | 11/2003 | Frey et al. |
| 2003/0215855 A1 | 11/2003 | Dubrow et al. |
| 2003/0215856 A1 | 11/2003 | Church et al. |
| 2003/0219781 A1 | 11/2003 | Frey |
| 2003/0224521 A1 | 12/2003 | Court et al. |
| 2004/0002103 A1 | 1/2004 | Short |
| 2004/0005673 A1 | 1/2004 | Jarrell et al. |
| 2004/0009479 A1 | 1/2004 | Wohlgemuth et al. |
| 2004/0009520 A1 | 1/2004 | Albert et al. |
| 2004/0014083 A1 | 1/2004 | Yuan et al. |
| 2004/0053362 A1 | 3/2004 | De Luca et al. |
| 2004/0096891 A1 | 5/2004 | Bennett |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0106728 A1 | 6/2004 | McGall et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0171047 A1 | 9/2004 | Dahl et al. |
| 2004/0185484 A1 | 9/2004 | Costa et al. |
| 2004/0229359 A1 | 11/2004 | Mead et al. |
| 2004/0241655 A1 | 12/2004 | Hwang et al. |
| 2004/0259146 A1 | 12/2004 | Friend et al. |
| 2005/0053997 A1 | 3/2005 | Evans |
| 2005/0069928 A1 | 3/2005 | Nelson et al. |
| 2005/0079510 A1 | 4/2005 | Berka et al. |
| 2005/0089889 A1 | 4/2005 | Ramsing et al. |
| 2005/0106606 A1 | 5/2005 | Parker et al. |
| 2005/0112574 A1 | 5/2005 | Gamble et al. |
| 2005/0118628 A1 | 6/2005 | Evans |
| 2005/0202429 A1 | 9/2005 | Trau et al. |
| 2005/0208503 A1 | 9/2005 | Yowanto et al. |
| 2005/0221340 A1 | 10/2005 | Evans |
| 2005/0227235 A1 | 10/2005 | Can et al. |
| 2005/0227316 A1 | 10/2005 | Santi et al. |
| 2005/0255477 A1 | 11/2005 | Can et al. |
| 2005/0287585 A1 | 12/2005 | Oleinikov |
| 2006/0003347 A1 | 1/2006 | Griffiths et al. |
| 2006/0008833 A1 | 1/2006 | Jacobson |
| 2006/0014146 A1 | 1/2006 | Sucaille et al. |
| 2006/0035218 A1 | 2/2006 | Oleinikov |
| 2006/0040297 A1 | 2/2006 | Leamon et al. |
| 2006/0054503 A1 | 3/2006 | Pamula et al. |
| 2006/0127920 A1 | 6/2006 | Church et al. |
| 2006/0127926 A1 | 6/2006 | Belshaw et al. |
| 2006/0134638 A1 | 6/2006 | Mulligan et al. |
| 2006/0160138 A1 | 7/2006 | Church et al. |
| 2006/0194214 A1 | 8/2006 | Church et al. |
| 2006/0281113 A1 | 12/2006 | Church et al. |
| 2006/0286678 A1 | 12/2006 | Dual et al. |
| 2007/0004041 A1 | 1/2007 | Church et al. |
| 2007/0122817 A1 | 5/2007 | Church et al. |
| 2007/0169227 A1 | 7/2007 | Cigan et al. |
| 2007/0231805 A1 | 10/2007 | Baynes et al. |
| 2007/0269870 A1 | 11/2007 | Church et al. |
| 2007/0281309 A1 | 12/2007 | Kong et al. |
| 2008/0003571 A1 | 1/2008 | McKernan et al. |
| 2008/0009420 A1 | 1/2008 | Schroth et al. |
| 2008/0044862 A1 | 2/2008 | Schatz et al. |
| 2008/0064610 A1 | 3/2008 | Lipovsek et al. |
| 2008/0105829 A1 | 5/2008 | Faris et al. |
| 2008/0214408 A1 | 9/2008 | Chatterjee et al. |
| 2008/0261300 A1 | 10/2008 | Santi et al. |
| 2008/0274510 A1 | 11/2008 | Santi et al. |
| 2008/0274513 A1 | 11/2008 | Shenderov et al. |
| 2008/0287320 A1 | 11/2008 | Baynes et al. |
| 2008/0300842 A1 | 12/2008 | Govindarajan et al. |
| 2009/0016932 A1 | 1/2009 | Curcio et al. |
| 2009/0036323 A1 | 2/2009 | Van Eijk et al. |
| 2009/0087840 A1 | 4/2009 | Baynes et al. |
| 2009/0093378 A1 | 4/2009 | Bignell et al. |
| 2009/0137408 A1 | 5/2009 | Jacobson |
| 2009/0155858 A1 | 6/2009 | Blake |
| 2009/0280497 A1 | 11/2009 | Woudenberg et al. |
| 2009/0280697 A1 | 11/2009 | Li et al. |
| 2009/0305233 A1 | 12/2009 | Borovkov et al. |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2010/0028873 A1 | 2/2010 | Belouchi et al. |
| 2010/0028885 A1 | 2/2010 | Balasubramanian et al. |
| 2010/0124767 A1 | 5/2010 | Oleinikov |
| 2010/0261158 A1 | 10/2010 | Nordman et al. |
| 2010/0273219 A1 | 10/2010 | May et al. |
| 2010/0311058 A1 | 12/2010 | Kim et al. |
| 2011/0117625 A1 | 5/2011 | Lippow et al. |
| 2011/0160078 A1 | 6/2011 | Fodor et al. |
| 2011/0172127 A1 | 7/2011 | Jacobson et al. |
| 2011/0217738 A1 | 9/2011 | Jacobson |
| 2011/0283110 A1 | 11/2011 | Dapkus et al. |
| 2011/0287490 A1 | 11/2011 | Coope et al. |
| 2012/0028843 A1 | 2/2012 | Ramu et al. |
| 2012/0115756 A1 | 5/2012 | Williams et al. |
| 2012/0185965 A1 | 7/2012 | Senger et al. |
| 2012/0220497 A1 | 8/2012 | Jacobson et al. |
| 2012/0270750 A1 | 10/2012 | Gen9 Inc |
| 2012/0270754 A1 | 10/2012 | Blake |
| 2012/0283110 A1 | 11/2012 | Shendure et al. |
| 2012/0283140 A1 | 11/2012 | Chu |
| 2012/0315670 A1 | 12/2012 | Jacobson et al. |
| 2012/0322681 A1 | 12/2012 | Kung et al. |
| 2013/0005582 A1 | 1/2013 | Lower |
| 2013/0017977 A1 | 1/2013 | Gen9 Inc |
| 2013/0059296 A1 | 3/2013 | Jacobson et al. |
| 2013/0059344 A1 | 3/2013 | Striedner et al. |
| 2013/0059761 A1 | 3/2013 | Jacobson et al. |
| 2013/0085083 A1 | 4/2013 | Kamberov et al. |
| 2013/0130347 A1 | 5/2013 | Delisa et al. |
| 2013/0196373 A1 | 8/2013 | Gregory et al. |
| 2013/0224729 A1 | 8/2013 | Church et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0163263 A1 | 10/2013 | Jacobson et al. |
| 2013/0274135 A1 | 10/2013 | Zhang et al. |
| 2013/0281308 A1 | 10/2013 | Kung et al. |
| 2013/0296192 A1 | 11/2013 | Jacobson |
| 2013/0296194 A1 | 11/2013 | Jacobson |

(56) References Cited

U.S. PATENT DOCUMENTS

| | | | |
|---|---|---|---|
| 2013/0309725 A1 | 11/2013 | Jacobson | |
| 2014/0141982 A1 | 5/2014 | Jacobson et al. | |
| 2014/0295556 A1 | 10/2014 | Joung et al. | |
| 2014/0309119 A1 | 10/2014 | Jacobson et al. | |
| 2015/0031089 A1 | 1/2015 | Lindstrom | |
| 2015/0045234 A1 | 2/2015 | Stone et al. | |
| 2015/0065393 A1 | 3/2015 | Jacobson | |
| 2015/0191719 A1 | 7/2015 | Hudson et al. | |
| 2015/0203839 A1 | 7/2015 | Jacobson et al. | |
| 2015/0315547 A1 | 11/2015 | Ixogen Ltd | |
| 2015/0368687 A1 | 12/2015 | Saaem et al. | |
| 2015/0376602 A1 | 12/2015 | Jacobson et al. | |
| 2016/0001247 A1 | 1/2016 | Oleinikov | |
| 2016/0097051 A1 | 4/2016 | Jacobson et al. | |
| 2016/0122755 A1 | 5/2016 | Hall et al. | |
| 2016/0144332 A1 | 5/2016 | Chu | |
| 2016/0144333 A1 | 5/2016 | Jacobson et al. | |
| 2016/0168564 A1 | 6/2016 | Jacobson et al. | |
| 2016/0215381 A1 | 7/2016 | Levine et al. | |
| 2016/0250613 A1 | 9/2016 | Jacobson et al. | |
| 2016/0326520 A1 | 11/2016 | Ramu et al. | |
| 2017/0137858 A1 | 5/2017 | Carr et al. | |
| 2017/0175110 A1 | 6/2017 | Jacobson et al. | |
| 2017/0198268 A1 | 7/2017 | Jacobson et al. | |
| 2017/0349925 A1 | 12/2017 | Jacobson et al. | |
| 2018/0023120 A1 | 1/2018 | Kung et al. | |

FOREIGN PATENT DOCUMENTS

| | | |
|---|---|---|
| CN | 101921840 | 12/2010 |
| DE | 4343591 | 6/1995 |
| EP | 0259160 | 3/1988 |
| EP | 1015576 | 7/2000 |
| EP | 1159285 | 12/2001 |
| EP | 1205548 | 5/2002 |
| EP | 1314783 | 5/2003 |
| EP | 1411122 | 4/2004 |
| EP | 2017356 | 1/2009 |
| EP | 2175021 | 4/2010 |
| JP | 2005-538725 | 12/2005 |
| JP | 2007-533308 A | 11/2007 |
| KR | 100491810 B1 | 11/2005 |
| WO | WO 1990/000626 A1 | 1/1990 |
| WO | WO 1992/015694 A1 | 9/1992 |
| WO | WO 1993/017126 | 9/1993 |
| WO | WO 1993/020092 | 10/1993 |
| WO | WO 1994/018226 | 8/1994 |
| WO | WO 1995/017413 | 6/1995 |
| WO | WO 1996/033207 | 10/1996 |
| WO | WO 1996/034112 | 10/1996 |
| WO | WO 1997/035957 | 10/1997 |
| WO | WO 1998/005765 | 2/1998 |
| WO | WO 1998/020020 | 5/1998 |
| WO | WO 1998/038299 | 9/1998 |
| WO | WO 1998/038326 | 9/1998 |
| WO | WO 1999/014318 | 3/1999 |
| WO | WO 1999/019341 | 4/1999 |
| WO | WO 1999/025724 | 5/1999 |
| WO | WO 1999/042813 | 8/1999 |
| WO | WO 1999/047536 | 9/1999 |
| WO | WO 2000/029616 | 5/2000 |
| WO | WO 2000/040715 | 7/2000 |
| WO | WO 2000/046386 | 8/2000 |
| WO | WO 2000/049142 | 8/2000 |
| WO | WO 2000/053617 A1 | 9/2000 |
| WO | WO 2000/075368 | 12/2000 |
| WO | WO 2001/081568 | 11/2001 |
| WO | WO 2001/085075 | 11/2001 |
| WO | WO 2001/088173 A2 | 11/2001 |
| WO | WO 2002/004597 A2 | 1/2002 |
| WO | WO 2002/024597 | 3/2002 |
| WO | WO 2002/081490 A2 | 10/2002 |
| WO | WO 2002/095073 A1 | 11/2002 |
| WO | WO 2002/101004 A2 | 12/2002 |
| WO | WO 2003/010311 A2 | 2/2003 |
| WO | WO 2003/033718 | 4/2003 |
| WO | WO 2003/040410 | 5/2003 |
| WO | WO 2003/044193 | 5/2003 |
| WO | WO 2003/046223 | 6/2003 |
| WO | WO 2003/054232 | 7/2003 |
| WO | WO 2003/060084 | 7/2003 |
| WO | WO 2003/064026 | 8/2003 |
| WO | WO 2003/064027 | 8/2003 |
| WO | WO 2003/064611 | 8/2003 |
| WO | WO 2003/064699 | 8/2003 |
| WO | WO 2003/065038 | 8/2003 |
| WO | WO 2003/066212 | 8/2003 |
| WO | WO 2003/083604 A2 | 10/2003 |
| WO | WO 2003/085094 | 10/2003 |
| WO | WO 2003/089605 A2 | 10/2003 |
| WO | WO 2003/100012 | 12/2003 |
| WO | WO 2004/002627 A2 | 1/2004 |
| WO | WO 2004/024886 | 3/2004 |
| WO | WO 2004/029586 | 4/2004 |
| WO | WO 2004/031351 | 4/2004 |
| WO | WO 2004/031399 | 4/2004 |
| WO | WO 2004/034028 A2 | 4/2004 |
| WO | WO 2004/090170 | 10/2004 |
| WO | WO 2005/059096 | 6/2005 |
| WO | WO 2005/071077 | 8/2005 |
| WO | WO 2005/089110 | 9/2005 |
| WO | WO 2005/103279 | 11/2005 |
| WO | WO 2005/107939 | 11/2005 |
| WO | WO 2005/123956 | 12/2005 |
| WO | WO 2006/031745 | 3/2006 |
| WO | WO 2006/044956 | 4/2006 |
| WO | WO 2006/049843 | 5/2006 |
| WO | WO 2006/076679 | 7/2006 |
| WO | WO 2006/086209 | 8/2006 |
| WO | WO 2006/127423 | 11/2006 |
| WO | WO 2007/008951 | 1/2007 |
| WO | WO 2007/009082 | 1/2007 |
| WO | WO 2007/010252 | 1/2007 |
| WO | WO 2007/075438 | 7/2007 |
| WO | WO 2007/087347 | 8/2007 |
| WO | WO 2007/113688 A2 | 10/2007 |
| WO | WO 2007/117396 | 10/2007 |
| WO | WO 2007/120624 | 10/2007 |
| WO | WO 2007/123742 | 11/2007 |
| WO | WO 2007/136736 | 11/2007 |
| WO | WO 2007/136833 A2 | 11/2007 |
| WO | WO 2007/136834 | 11/2007 |
| WO | WO 2007/136835 | 11/2007 |
| WO | WO 2007/136840 | 11/2007 |
| WO | WO 2008/024319 | 2/2008 |
| WO | WO 2008/027558 | 3/2008 |
| WO | WO 2008/041002 | 4/2008 |
| WO | WO 2008/045380 | 4/2008 |
| WO | WO 2008/054543 | 5/2008 |
| WO | WO 2008/076368 | 6/2008 |
| WO | WO 2008/109176 | 9/2008 |
| WO | WO 2008/130629 | 10/2008 |
| WO | WO 2009/032167 | 3/2009 |
| WO | WO2010/025310 A2 | 3/2010 |
| WO | WO 2010/070295 | 6/2010 |
| WO | WO 2010/115100 | 10/2010 |
| WO | WO 2010/115154 A1 | 10/2010 |
| WO | WO 2011/056872 | 5/2011 |
| WO | WO 2011/066185 | 6/2011 |
| WO | WO 2011/066186 | 6/2011 |
| WO | WO 2011/085075 | 7/2011 |
| WO | WO 2011/143556 | 11/2011 |
| WO | WO 2011/150168 | 12/2011 |
| WO | WO 2011/161413 | 12/2011 |
| WO | WO 2012/064975 | 5/2012 |
| WO | WO 2012/078312 | 6/2012 |
| WO | WO 2012/084923 | 6/2012 |
| WO | WO 2012/174337 | 12/2012 |
| WO | WO 2013/032850 | 3/2013 |
| WO | WO 2013/163263 | 10/2013 |
| WO | WO 2014/004393 | 1/2014 |
| WO | WO 2014/089290 A1 | 6/2014 |
| WO | WO 2014/093694 | 6/2014 |
| WO | WO 2014/144288 A1 | 9/2014 |

(56) References Cited

FOREIGN PATENT DOCUMENTS

| WO | WO 2014/151696 | 9/2014 |
|---|---|---|
| WO | WO 2014/160004 | 10/2014 |
| WO | WO 2014/160059 | 10/2014 |
| WO | WO 2014/191518 A1 | 12/2014 |
| WO | WO 2015/017527 | 2/2015 |
| WO | WO 2015/035162 A2 | 3/2015 |
| WO | WO 2015/081114 | 6/2015 |

OTHER PUBLICATIONS

Williams et al., "Modifying the stereochemistry of an enzyme-catalyzed reaction by directed evolution", PNAS, vol. 100, No. 6, pp. 3143-3148, Mar. 18, 2001.
Office Action in U.S. Appl. No. 13/799,039 dated Sep. 25, 2014.
Gasiunas et al., Cas9-crRNA ribonucleoprotein complex mediates specific DNA cleavage for adaptive immunity in bacteria. Proc Natl Acad Sci U S A. 2012 Sep 25;109(39):E2579-86. Epub 2012 Sep 4.
Jinek et al., A programmable dual-RNA-guided DNA endonuclease in adaptive bacterial immunity. Science. 2012 Aug 17;337(6096):816-21. doi: 10.1126/science.1225829. Epub 2012 Jun 28.
Nakayama et al., A system using convertible vectors for screening soluble recombinant proteins produced in Escherichia coli from randomly fragmented cDNAs, Biochem. Biophys. Res. Comm., 2003 Dec 19; 312(3):825-830.
Pemov et al., DNA analysis with multiplex microarray-enhanced PCR. Nucleic Acids Res. Jan. 2005 20;33(2):e11.
Saha et al., The promoter of the Chinese hamster ovary dihydrofolate reductase gene regulates the activity of the local origin and helps define its boundaries. Genes Dev. 2004 Feb 15;18(4):397-410. Epub 2004 Feb 20.
Third Party Observation under Article 115 EPC for EP publication No. 2864531, dated May 18, 2018.
Weiner et al., Kits and their unique role in molecular biology: a brief retrospective. Biotechniques. Apr. 2005;44(5):701-4. doi: 10.2144/000112796.
Yosef et al., Restoration of gene function by homologous recombination: from PCR to gene expression in one step. Appl Environ Microbiol. Dec. 2004;70(12):7156-60.
U.S. Appl. No. 13/986,366, filed Apr. 24, 2013, Inventor Jacobson et al.
U.S. Appl. No. 13/986,368, filed Apr. 24, 2013, Inventor Kung et al.
U.S. Appl. No. 13/592,827, Aug. 23, 2012, Inventor Jacobson et al.
U.S. Appl. No. 14/241,242, Nov. 14, 2014, Inventor Jacobson et al.
U.S. Appl. No. 15/521,087, Apr. 21, 2017, Inventor Jacobson et al.
U.S. Appl. No 13/884,446, Jul. 29, 2013, Inventor Jacobson et al.
U.S. Appl. No. 15/324,522 Jan. 6, 2017, Inventor Jacobson et al.
U.S. Appl. No. 14/402,103, Dec. 15, 2014, Inventor Hudson et al.
U.S. Appl. No. 13/505,376, Jun. 19, 2012, Inventor Jacobson et al.
U.S. Appl. No. 11/897,939, filed Aug. 31, 2007, Inventor Blake.
U.S. Appl. No. 13/250,083, filed Sep. 30, 2011, Inventor Blake.
U.S. Appl. No. 13/884,463, filed, Jul. 18, 2013, Inventor Jacobson et al.
U.S. Appl. No. 15/054,038, Feb. 25, 2016, inventor Jacobson et al.
U.S. Appl. No. 13/524,164, filed Jun. 15, 2012, Inventor Kung et al.
U.S. Appl. No. 15/666,345, filed Aug. 1, 2017, Inventor Kung et al.
U.S. Appl. No. 15/039,620, filed May 26, 2016, Inventor Jacobson et al.
U.S. Appl. No. 13/799,039, filed Mar. 13, 2013, Inventor Hudson et al.
Abremski et al. Studies on the properties of P 1 site-specific recombination: evidence for topologically unlinked products following recombination. Cell 32:1301-1311 (1983).
Abremski K. et al. Bacteriophage Pl site-specific recombination. Purification and properties of the Cre recombinase protein (1984) J. Mol. Biol. 259: 1509-1514.
Adessi et al., Solid phase DNA amplification: characterisation of primer attachment and amplification mechanisms, Nucleic Acids Research, 28(20):E87, (Oct. 15, 2000).

Afshari et al. Application of Complementary DNA Microarray Technology to Carcinogen Identification, Toxicology, and Drug Safety. Cancer Research, 59, 4759-4760, Oct. 1, 1999.
Aihara, H. et al. A Conformational Switch Controls the DNA Cleavage Activity of .lamda. Integrase, Molecular Cell, 12:187-198, (Jul. 2003).
Akhundova A.A. et al. RNA synthesis on immobilized DNA templates in vitro. Biochemistry-Moscow, 43(5):626-628 (1978).
Altschul et al., Iterated profile searches with PSI-BLAST —a tool for discovery in protein databases, Trends Biochem. Sci., 23:444-447, (Nov. 1998).
Altschul, S., et al. Basic local alignment search tool, J Mol Biol., 215(3):403-10, (1990).
Andersen, J., et al. New Unstable Variants of Green Fluorescent Protein for Studies of Transient Gene Expression in Bacteria, Applied and Environmental Microbiology, 64(6):2240-2246 (Jun. 1998).
Ashkin, A., Applications of laser radiation pressure Science, 210(4474): 1081-1088, (Dec. 5, 1980).
Aslanzadeh, Brief Review: Preventing PCR Amplification Carryover Contamination in a Clinical Laboratory. Annals of Clinical & Laboratory Science 34(4) :389 (2004).
Au, L., et al. Gene Synthesis by a LCR-Based Approach: High. cndot.Level Production of Leptin-L54 Using Synthetic Gene in Escherichia coli , Biochemical and Biophysical Research Communications, 248:200-203 (1998).
Babineau et al. The FLP Protein of the 2 micron Plasmid of Yeast (1985) J. Biol. Chem. 260: 12313-12319.
Bar G., et al., Dendrimer-modified silicon oxide surfaces as platforms for the deposition of gold and silver colloid monolayers: preparation method, characterization, and correlation between microstructure and optical properties, Langmuir, 12(5): 1172-1179, (Mar. 6, 1996).
Bartsevich, V., et al. Engineered Zinc Finger Proteins for Controlling Stem Cell Fate, Stem Cells, 21:632-637 (2003).
Beer, N., et al., On-chip, real time single-copy polymerase chain reaction in picoliter droplets, Analytical Chemistry, 79(22):8471-8475, (Nov. 15, 2007).
Beier et al., Analysis ofDNA-microarray produced by inverse in situ oligonucleotide synthesis. J. Biotechnology, 94:15-22 (2002).
Bennett, S., Solexa Ltd., Pharmacogenomics, 5(4):433-8, (Jun. 2004).
Berlin Y. A. DNA splicing by directed ligation (SDL), Current Issues Molec. Biol. 1:21-30, 1999.
Bethell, D., et al. From monolayers to nanostructured materials: an organic chemist's view of self-assembly, J. Electroanal. Chem., 409:137-143, (1996).
Binkowski B. F. et al. Correcting erros in synthetic DNA through consensus shuffling Nucl. Acids Res., vol. 33, No. 6, e55, 2005.
Blanchard, A., Synthetic DNA Arrays, Genetic Engineering, 20:111-123, Plenum Press, (1998).
Boal, J., et al. Cleavage of oligodeoxyribonucleotides from controlled-pore glass supports and their rapid deprotection by gaseous amines, Nar, 24(15):3115-3117, (1996).
Boltner, D., et al. R391: A Conjugative Integrating Mosaic Comprised of Phage, Plasmid, and Transposon Elements, J. Of Bacteriology, 184(18):5158-5169 (Sep. 2002).
Booth, P., et al. Assembly and cloning of coding sequences for neurotrophic factors directly from genomic DNA using polymerase chain reaction and uracil DNA glycosylase, Gene, 146(2):303308 (1994).
Braatsch et al., Escherichia coli strains with promoter libraries constructed by Red/ET recombination pave the way for transcriptional fine-tuning, Biotechniques. 45(3): 335-337 (2008).
Brown, C. BioBricks to help reverse-engineer life, URL: http://eetimes.com/news/latest/showArticle.ihtml?articleID=21700333, (Jun. 11, 2004).
Burge et al., Prediction of complete gene structures in human genomic DNA, J Mol Biol., 268(1):78-94, (1997).
Cai, Q., et al. Immunogenicity of Polyepitope Libraries Assembled by Epitope Shuffling: An Approach to the Development of Chimeric Gene Vaccination Against Malaria, Vaccine, 23:267-277, (2004).

(56) References Cited

OTHER PUBLICATIONS

Carr, P., et al. Protein-mediated error-correction for de novo DNA synthesis, Nucleic Acids Research, 32(20), e162 (9 pages), (2004).
Caruthers, et al. CXV. Total synthesis of the structural gene for an alanine transfer RNA from yeast. Enzymic joining to form the total DNA duplex, J Mol Biol., 72(2):475-92, (Dec. 28, 1972).
Cassell et al., Mechanism of Inhibition of Site-specific Recombination by the Holliday Junction-trapping Peptide WKHYNY: Insights into Phage I integrase-mediated Strand Exchange, J. Mol. Biol., 327:413-429, (2003).
Chakrabarti et al., Novel Sulfoxides facilitate GC-rich template amplification., 2002, BioTechniques 32(4):866-873.
Chalmers et al., Scaling up the ligase chain reaction-based approach to gene synthesis, BioTechniques, 30(2):249-252, (Feb. 2001).
Chan, L. et al. Refactoring bacteriophage T7, Molecular Systems Biol., doi: 10.1038/msb4100025, (Published online Sep. 13, 2005).
Chandrasegaran, S., et al. Chimeric Restriction Enzymes: What is Next?, Biol. Chem., 380:841848 (1999).
Chang, C., et al. Evolution of a cytokine using DNA family shuffling, NatureBiotechnology, 17: 793- 797(1999).
Che, A. BioBricks++: Simplifying Assembly of Standard DNA Components, [Online] XP002412778, URL: http://austinche.name/docs/bbpp.pdf, (Jun. 9, 2004).
Chen, H., et al. A new method for the synthesis of a structural gene, Nucleic Acids Research, 18(4):871-878 (Feb. 1990).
Cherepanov, A., et al. Joining of short DNA oligonucleotides with base pair mismatches by T4 DNA ligase, J Biochem., 129(1):61-68, (Jan. 2001).
Chetverin et al., Sequencing pool of Nucleic Acids on Oligonucleotide arrays, Biosystems, 30:215231, (1993).
Chevalier et al., Homing endonucleases: structural and functional insight into the catalysts of intron/intein mobility, Nucl. Acids Res., 29(18):3757-3774 (2001).
Chevalier, B., et al. Design, Activity, and Structure of a Highly Specific Artificial Endonuclease, Molecular Cell, 10:895-905 (Oct. 2002).
Cho, S., et al. Creating, transporting, cutting and merging liquid droplets by electrowetting-based actuation for digital microfluidic circuits, J. Of Microelectromechanical Systems, 12(1):70-80, (Feb. 2003).
Christians, F., et al. Directed evolution of thymidine kinase for AZT phosphorylation using DNA family shuffling, Nature Biotechnology, 17:259-264(1999).
Coco, W., et al. Growth Factor Engineering by Degenerate Homoduplex Gene Family Recombination, Nature Biotechnology, 20:1246-1250, (Dec. 2002).
Colvin, V., et al. Semiconductor nanocrystals covalently bound to metal surfaces with self-assembled monolayers, J. Am. Chem. Soc., 114(13):5221-5230, 1992.
Crameri, A, et al. DNA shuffling of a family of genes from diverse species accelerates directed evolution, Nature, 391:288-291(1998).
Crameri, A, et al. Molecular evolution of an arsenate detoxification pathway by DNA shuffling, Nature Biotechnology, 15:436-438 (1997).
Crameri, A., et al. Improved Green Fluorescent Protein by Molecular Evolution Using DNA Shuffling, Nature Biotechnology, 14:315-319, (Mar. 1996).
Cui T. et al. Sepharose-supported DNA as template for RNA synthesis J. Biotechnology, 66: 225-228 (1998).
Dafhnis-Calas, F., et al. Iterative in vivo assembly of large and complex transgenes by combining the activities of <DC31 integrase and Cre recombinase, Nucleic AcidsResearch, 33(22): 1-14 (2005).
Datsenko K.A. et al. One-step inactivation of chromosomal genes in *Escherichia coli* K-12 using PCR products PNAS (2000) 97: 6640-6645.
Dedkova, L. et al. Enhanced D-Amino Acid Incorporation into Protein by modified Ribosomes, J. Am. Chem. Soc., 125:6616-6617, (2003).
Dillon, P.J. et al., A Rapid Method for the Construction of Synthetic Genes Using the Polymerase Chain Reaction, Biotechniques, vol. 9, No. 3, pp. 298-300, 1990.
Doyon et al., Enhancing zinc-finger-nuclease activity with improved obligate heterodimeric architectures. Nat Methods. 2011 Jan;8(1):74-9. doi:10.1038/nmeth.1539. Epub Dec. 5, 2010.
Duggan et al., Expression Profiling Using cDNA Microarrays, Nat. Genet. S21:10-14 (1999).
Ellson, Picoliter: Ennabling Precise Transfer of Nanoliter and Picoliter Volumes. Drug Discovery Today 7(5 Suppl.) :s32 (2002).
Elowitz et al., A synthetic oscillatory network of transcriptional regulators. Nature. 2000;403;335-338.
Engler C. et al. A one pot, one step, precision cloning method with high throughput capability PLoS One, 3: e36471.
Engler C. et al. Golden Gate Shuffling: a one-pot DNA shuffling method based on type IIS restriction enzymes PLoS One, 4:e5553, 2009.
Evans et al., Roles for Mismatch Repair Factors in Regulating Genetic Recombination, Molecular & Cellular Biology, 20(21):7839-7844 (Nov. 2000).
Ferretti, L. et al. Total synthesis of a gene for bovine rhodopsin, PNAS, 83:599-603 (Feb. 1986).
Ferrin, L.J., et al. Sequence-specific ligation of Dna using RecA protein, Proc. Natl. Acad. Sci. USA, 95: 2152-2157 (1998).
Fidalgo et al., Surface induced droplet fusion in microfluidic devices, Lab on Chip, 7(8)984-986, (2007).
Fisch, I. et al. A Strategy of Exon Shuffling for Making Large Peptide Repertoires Displayed on Filamentous Bacteriophage, Proceedings of the National Academy of Sciences of USA, 93:77617766, (Jul. 1996).
Flanagan et al. Analysis of inhibitors of the site-specific recombination reaction mediated by Tn3 resolvase (1989) J. Mol. Biol. 206: 295-304.
Fleck et al., DNA Repair, J. Cell Science, 117(4):515-517 (2004).
Fodor, S., et al., Light-directed, spatially addressable parallel chemical synthesis, Science, 251(4995):767-773, (Feb. 15, 1991).
Fujita et al., Surprising liability of biotin-streptavidin bond during transcription of biotinylated DNA bound to paramagnetic streptavidin beads. Bio Techniques, 14:608-617 (1993).
Fullwood et al., (2009) www.genome.org/cgi/doi/10.1101/gr.074906.107.
Gabsalilow et al., Site- and strand-specific nicking of DNA by fusion proteins derived from MutH and I-SceI or TALE repeats. Nucleic Acids Res. 2013 Apr;41(7):e83. doi: 10.1093/nar/gkt080. Epub Feb. 13, 2013.
Gao, X. et al. Thermodynamically balanced inside-out (TBIO) PCR-based gene synthesis: a novel method of primer design for high fidelity assembly of longer gene sequences, Nucleic Acids Research, 31(22):e143 (11 pages) (2003).
Gardner, T., et al. Construction of a genetic toggle switch in *Escherichia coli* , Nature, 403(20):339-342 (Jan. 2000).
Gibbs, W. Synthetic Life, Scientific American, [Online] URL: http://www.sciam.com/orintversion.cfm?articleID=0009FCA4, (Apr. 26, 2004).
Glasgow A.C. et al. DNA-binding properties of the Hin recombinase (1989) J. Biol. Chem. 264: 10072-10082.
Goler, J. BioJADE: A Design and Simulation Tool for Synthetic Biological Systems, MIT Computer Science and Artificial Intelligence Laboratory, AI Technical Report, [Online] URL:http://dspace.mit.edu/bitstream/1721.1/30475/2/MIT-CSAIL-TR-2004-036.pdf, (May 2004).
Grabar, K., et al., Preparation and Characterization Monolayers, Anal. Chem., 67:735- 743, (1995).
Greenberg et al., Cleavage of oligonucleotides from solid-phase support using o-nitrobenzyl photochemistry, J. of Org. Chem., 59(4):746-753, (Feb. 1994).
Grifith et al., Coordinating Multiple Droplets in Planar Array Digital Microfluidic Systems, The International Journal of Robotics Research, 24(11):933-949, (Nov. 2005).
Gronostajski et al., The FLP protein of the 2 micron plasmid of yeast (1985) J. Biol. Chem. 260: 12328-12335.

(56) References Cited

OTHER PUBLICATIONS

Guilinger et al., Fusion of catalytically inactive Cas9 to FokI nuclease improves the specificity of genome modification. Nat Biotechnol. 2014 Jun;32(6):577-582. doi: 10.1038/nbt.2909. Epub Apr. 25, 2014.
Gulati S. et al. Opportunities for microfluidic technologies in synthetic biology. Journal of the Royal Society, vol. 6, Suppl. 4, pp. S493-S506, (2009).
Guntas, G., et al. A molecular switch created by in vitro recombination of nonhomologous genes, Chem. & Biol., 11:1483-1487 (Nov. 2004).
Guntas, G., et al. Directed Evolution of Protein Switches and Their Application to the Creation of Ligand-Binding Proteins, Proc. Natl. Acad. Sci. USA, 102(32):11224-11229 (Aug. 9, 2005).
Gupta, N., et al. Studies on Polynucleotides, LXXXVIII. Enzymatic Joining of Chemically Synthesized Segments Corresponding to the Gene for Alanine-tRNA, PNAS, 60:1338-1344, (1968).
Hacia J.G. et al. Applications of DNA chips for genomic analysis. Mol Psychiatry. Nov. 1998; 3(6):483-92.
Hacia J.G. Resequencing and mutational analysis using oligonucleotide microarrays, Nature Genetics, 21(1 suppl):42-47, 1999.
Haeberle et al., Microfluidic platforms for lab-on-chip applications, Lab on a Chip 7(9):1094-1110, (2007).
Haffter et al. Enhancer independent mutants of the Cin recombinase have a relaxed topological specificity. (1988) EMBO J. 7:3991-3996.
Hansen et al., Review of Mammalian DNA Repair and Transcriptional Implications, J. Pharmacol. & Exper. Therapeutics, 295(1):1-9, (2000).
Hardy, P., et al., Reagents for the preparation of two oligonucleotides per synthesis (TOPSTM), Nucleic Acids Research, 22(15):2998-3004, (1994).
Hawley et al., Compilation and analysis of *Escherichia coli* promoter DNA sequences Nucl. Acid. Res. 11:2237-2255. 1983.
Hecker, K. Error Analysis of Chemically Synthesized Polynucleotides, BioTechniques, 24(2):256260, (Feb. 1998).
Heeb, S., et al. Small, Stable Shuttle Vectors Based on the Minimal pVS1 Replicon for Use in Gram-Negative Plant-Associated Bacteria, MPMI, 13(2):232-237 (2000).
Henegariu et al. Multiplex PCR: critical parameters and step-by-step protocol Biotechniques, 23(3): 504-511, (Sep. 1997).
Hermeling, S., et al. Structure-Immunogenicity Relationships of Therapeutic Proteins, Pharmaceutical Research, 21(6):897-903, (Jun. 2004).
Higuchi, R., et al. A general method of in vitro preparation and specific mutagenesis of DNA fragments: study of protein and DNA interactions, Nucleic Acids Research, 16(15):7351-7367 (1988).
Hoess et al., Mechanism of strand cleavage and exchange in the Cre-lox site-specific recombination system (1985) J. Mol. Biol. 181: 351-362.
Hoess R.H. et al. Interaction of the bacteriophage P 1 recombinase Cre with the recombining site loxP (1984) Proc. Natl. Acad. Sci. USA 81: 1026-1029.
Hoess R.H. et al. P 1 site-specific recombination: nucleotide sequence of the recombining sites (1982) Proc. Natl. Acad. Sci. USA 79: 3398-3402.
Hoess R.H. et al. The role of the loxP spacer region in PI site-specific recombination (1986), Nucleic Acids Res. 14: 2287-2300.
Holmes, C., Model studies for new o-nitrobenzyl photolabile linkers: substituent effects on the rates of photochemical cleavage, J. Of Org. Chem., 62(8):2370-2380, (Apr. 18, 1997).
Hoover et al., DNAWorks: an automated method for designing oligonucleotides for PCR-based gene synthesis, Nucleic Acids Research, 30(10):e43 (7 pages), (2002).
Horton, R., et al. Engineering hybrid genes without the use of restriction enzymes: Gene splicing by overlap extension, Gene, 77:61-68, (1989).
Hyman, E., A new method of sequencing DNA, Analytical Biochemistry, 174(2):423-436, (Nov. 1, 1988).
Ibrahim, E., et al. Serine/arginine-rich protein-dependent suppression of exon skipping by exonic splicing enhancers, Proc. Natl. Acad. Sci. U S A, 102(14):5002-5007, (Apr. 5, 2005).
Ito R. et al. Novel muteins of human tumor necrosis factor alpha Biochimica et Biophysica Acta, 1096 (3): 245-252 (1991).
Jayaraman et al. Polymerase chain-reaction mediated gene synthesis: synthesis of a gene coding for Isozyme C of Horseradish Peroxidase Pnas 88:4084-4088, (May 1991).
Jayaraman, et al. A Pcr-mediated Gene synthesis strategy involving the assembly of oligonucleotides representing only one of the strands, Biotechniques, 12(3):392-398, (1992).
Jensen P.R. et al. The sequence of spacers between the consensus sequences modulates the strength of prokaryotic promoters Appl. Env. Microbiol. 64:82-87, 1998.
Johnston M. Gene chips: Array of hope for understanding gene regulation. Current Biology, 8: (5) R171, 1998.
Jones, T.D., et al. The Development of a Modified Human IFN-alpha2b Linked to the Fc Portion of Human IgG1 as a Novel Potential Therapeutic for the Treatment of Hepatitis C Virus Infection, Journal of Interferon & Cytokine Research, 24:560-572,(2004).
Kahl, J., et al. Solution-Phase Bioconjugate Synthesis Using Protected Oligonucleotides Containing 3'-Alkyl Carboxylic Acids, J. Of Org. Chem., 64(2):507-510, (1999).
Kahl, J., et al., High-Yielding Method for On-col. Derivatization of Protected Oligodeoxy-nucleotides and Its Application to the Convergent Synthesis of 5',3'-Bis-conjugates, J. Of Org. Chem., 63(15):4870-.
Kampke et al., Efficient primer design algorithms. Bioinformatics, 2001;17(3):214-225.
Kelly, B., et al., Miniaturizing chemistry and biology in microdroplets, Chem. Commun., 17731788, (2007).
Khaitovich, P., et al. Characterization of functionally active subribosomal particles from Thermus aquaticus, Proc. Natl. Acad. Sci., 96:85-90 (Jan. 1999).
Kim et al., Precision genome engineering with programmable DNA-nicking enzymes. Genome Res. 2012 Jul;22(7):1327-33. doi:10.1101/gr.138792.112. Epub 2012 Apr. 20.
Kim J.H. et al. Solid-phase genetic engineering with DNA immobilized on a gold surface. J. Biotechnology, 96:213-221. (2002).
Kim, C., et al. Biological lithography: Improvements in DNA synthesis methods, J. Vac. Sci. Technol. B 22(6):3163-3167 (2004).
Kim, Y., et al. Insertion and Deletion Mutants of FokI Restriction Endonuclease, J. Biol. Chem., 269(50):31978-31982 (1994).
Kinde et al., Detection and quantification of rare mutations with massively parallel sequencing. Proc Natl Acad Sci U S A. 2011 Jun 7;108(23):9530-5. doi: 10.1073/pnas.1105422108. Epub 2011 May 17. Supplemental Information.
Kisselev, L., et al. Termination of translation: interplay of mRNA, rRNAS and release factors?, the Embo J., 22(2):175-182, (2003).
Kitamura, Koichiro et al. Construction of Block-Shuffled Libraries of DNA for Evolutionary Protein Engineering: Y-Ligation-Based Block Shuffling. Protein Engineering, 15(10): 843-853, (Oct. 2002).
Kleppe K., et al. Studies of polynucleotides: repair replication of short synthetic DNA's as catalyzed by DNA polymerases, J. Mol. Biol. 56:341-361, (1971).
Kodumal., S., et al. Total synthesis of long DNA sequences: Synthesis of a contiguous 32-kb polyketide synthase gene cluster, Pnas, 101(44):15573-15578, (Nov. 2, 2004).
Kolisnychenko, V., et al. Engineering a Reduced Escherichia coli Genome, Genome Research, 12:640-647, (2002).
Kong, D., et al., Parallel gene synthesis in microfluidic device, Nucleic Acids Research, vol. 35, No. 8, pp. e61-1 (9 pages), (2007).
Kosuri et al. (Scalable gene synthesis by selective amplification of DNA pools from high-fidelity microchips, Nature Biotechnology 28, 1295-1299 (2010), Published online Nov. 28, 2010).
Kotsopoulou, E., et al. A Rev-Independent Human Immunodeficiency Virus Type 1 (HIV-1)-Based Vector That Exploits a Codon-Optimized HIV-1 gag-pol Gene, Journal of Virology, 74(10):4839-4852, (May 2000).
Kowalczykowski, S. In vitro reconstitution of homologous recombination reactions, Experientia, 50:204-215, (1994).

(56) References Cited

OTHER PUBLICATIONS

Kowalczykowski, S. Initiation of genetic recombination and recombination-dependent replication, TIBS, 25:156-165, (Apr. 2000).
Krieg et al., Real-time detection of nucleotide incorporation during complementary DNA strand analysis Chem. Bio. Chem. 4:589-592 (2003).
Kurian et al. DNA chip technology. J Pathol.; 187(3):267-71, (Feb. 1999).
Lamers, M., et al. ATP Increases the Affinity between MutS ATPase Domains, J. Biol. Chem., 279(42):43879-43885, (Oct. 15, 2004).
Lashkari et al. An automated multiplex oligonucleotide synthesizer: Development of high throughpout, low cost Dna synthesis. Pnas 92(17): 7912-7915, (1995).
Leamon, J., et al., A massively parallel PicoTiterPlate.TM.based platform for discrete picoliter-scale polymerase chain reactions, Electrophoresis, 24(21):3769-3777, (Nov. 2003).
Lebedenko E.N. et al. Method of artificial DNA splicing by directed ligation Nucleic Acids Research, 19: 6757-6761, 1991.
Lee, K., et al. Genetic approaches to Studying Protein Synthesis: Effects of Mutations at .psi.1516 and A535 in *Escherichia coli* 16S rRNA, J. Nutr., 131:2994S-3004S, (2001).
Leslie et al., Site-specific recombination in the replication terminus region of *Escherichia coli* : functional replacement of dif. (1995) EMBO J. 14: 1561-1570.
Lewis et al. Gene modification via plug and socket gene targeting. J Clin Invest. 1996 Jan 1;97(1):3-5.
Lewis et al., Control of directionality in intergrase-mediated recombination: examination of recombination directionality factors (RDFs) including Xis and Cox proteins, Nucl. Acids Res., 29(11):2205-2216 (2001).
Li et al., Alteration of the cleavage distance of Fok I restriction endonuclease by insertion mutagenesis. Proc Natl Acad Sci U S A, 90:2764-2768, (Apr. 1993).
Li et al., Ligation independent cloning irrespective of restriction site compatibility, Nucl. Acids Res., 25(20):4165-4166, (1997).
Link, a., et al. Methods for generating precise deletions and insertions in the genome of wild-type *Escherichia coli* : Application to open reading frame characterization, J. Bacteriol., 179(20):6228-6237, (Oct. 1997).
Liu G. et al. DNA computing on surfaces. Nature, 403: 175-179 (2000).
Liu, W. et al. Genetic Incorporation of Unnatural Amino Acids Into Proteins in Mammalian Cells, Nature Methods, 4(3):239-244, (Mar. 2007).
Liu, Y., et al., DNA ligation of ultramicrovolume using EWOD microfluidic system with coplanar electrodes: DNA ligation of ultramicrovolume using a EWOD microfluidic system, J. of Micromechanics and Microengineering, 18(4):45017 (7 pages), (2008).
Lu et al., Conjugative transposition: Tn916 integrase contains two independent DNA binding domains that recognize different DNA sequences '(1994) EMBO J. 13: 1541-1548.
Luo, P., et al. Development of a Cytokine Analog with Enhanced Stability Using Computational Ultrahigh Throughput Screening, Protein Science, 11:1218-1226, (2002).
Lutz, S., et al. Homology-Independent Protein Engineering, Current Opinion in Biotechnology, 11(4):319-324, (Aug. 2000).
Mandecki et al. Fold method of gene synethsis Gene, 68:101-107 (1988).
Mandecki W. Oligonucleotide-directed double-strand break repair in plasmids of *Escherichia coli*: A method for site-specific mutagenesis. 1986, PNAS, 83 :7177-7181.
Mannervik, B. Optimizing the Heterologous Expression of Glutathione Transferase, Methods in Enzymology, 401:254-265, (2005).
Margulies et al., Genome Sequencing in Microfabricated High-Density Picolitre Reactors, Nature. 437: 376-380 (2005). Supplemental materials.
Matzas et al. (High-fidelity gene synthesis by retrieval of sequence-verified Dna identified using high-throughput pyrosequencing, Nature Biotechnology 28, 1291-1294 (2010), Published online.
McCaughan et al., Single-molecule genomics. J Pathol. 2010 Jan;220(2):297-306. doi: 10.1002/path.2647.
McClain et al., Genome Sequence Analysis of Helicobacter Pylori Strains Associated with Gastric Ulceration and Gastric Cancer, BMC Genomics, Biomed Central Ltd, London, IK. 10(1):3 (2009).
McGall et al., Light-Directed Synthesis of High-Density Oligonucleotide Arrays Using Semiconductor Photoresists, Pro. Natl. Acad. Sci. 93(24):13555-13560 (1996).
Mei et al., Cell-Free Protein Synthesis in Microfluidic Array Devices, Biotechnol. Prog. 2007, 23:1305-1311.
Mercier. J. et al. Structural and functional characterization of tnpI, a recombinase locus in Tn21 and related beta-lactamase transposons. (1990) J. Bacteriol. 172: 3745.
Metzker, Emerging technologies in DNA sequencing. Genome Res. 2005 Dec;15(12):1767-76.
Metzker, M., et al., Termination of DNA synthesis by novel 3'-modified-deoxyribonucleoside 5'-triphosphates, NAR, 22(20):4259-4267, (1994).
Meyer-Leon et al. Purification of the FLP site-specific recombinase by affinity chromatography and re-examination of basic properties of the system (1987) Nucleic Acids Res. 15: 6469.
Mezard, C., et al. Recombination Between Similar But Not Identical DNA Sequences During Yeast Transformation Occurs Within Short Stretches of Identity, Cell, 70:659-670, (Aug. 21, 1992).
Miick, S., et al. Crossover isomer bias is the primary sequence-dependent property of immobilized Holliday junctions, Proc. Natl. Acad. Sci. USA, 94:9080-9084, (Aug. 1997).
Milton, R., et al. Total Chemical Synthesis of a D-Enzyme: the Enantiomers of HIV-1 Protease Show Demonstration of Reciprocal Chiral Substrate Specificity, Science, 256:1445-1448, (Jun. 5, 1992).
Mir K. U. et al. Sequencing by cyclic ligation and cleavage (CycLic) directly on a microarray captured template. Nucl. Acids Rse. vol. 37, No. 1 e5, 2008.
Mitra et al., Fluorescent in situ Sequencing on Polymerase Colonies, Analytical Biochemistry. 320:55-65 (2003).
Modrich, P. Strand-specific Mismatch Repair in Mammalian Cells, J. Biol. Chem., 272(40): 24727-24730, (Oct. 3, 1997).
Moffitt et. al. Recent Advances in Optical Tweezers. Annual Review of Biochemistry 77 :205 (Feb. 2008).
Moore et al., Computational Challenges in Combinatorial Library Design for Protein Engineering, AIChE Journal, 50(2):262-272, (Feb. 2004).
Morton, Life, Reinvented. Wired. 2009. Retrieved from http://archive.wired.com/wired/archive/13.01/mit _pr.html on Aug. 14, 2015.
Muller, Ten years of gene targeting: targeted mouse mutants, from vector design to phenotype analysis. Mech Dev. 1999 Apr;82(1-2):3-21.
Nakamaye, K., et al. Direct sequencing of polymerase chain reaction amplified Dna fragments through the incorporation of deoxynucleoside-thiotriphosphates, Nucleic Acids Research, 16(21):9947-9959, (1988).
Nakamura et al., How protein reads the stop codon and terminates translation, Genes to Cells, 3:265-278, (1998).
Ness, J., et al. DNA shuffling of subgenomic sequences of subtilisin, Nature Biotechnology 17: 893-896 (1999). Abstract only.
Ness, J., et al. Synthetic Shuffling Expands Functional Protein Diversity by Allowing Amino Acids to Recombine Independently Nature Biotechnology, 20:1251-1255, (Dec. 2002).
Neuman et al., Optical trapping. Rev Sci Instrum. 2004 Sep;75(9):2787-809.
Nilsson P., et al. Real-Time monitoring of DNA manipulations using biosensor technology, Analytical Biochemistry, 224:400-408, (1995).
Nilsson, L., et al. Improved Heterologous Expression of Human Glutathione Transferase A4-4 by Random Silent Mutagenesis of Codons in the 5'Region, Biochemica et Biophysica Acta, 1528: 101-106, (2001).
Noirot et al., DNA Strand Invasion Promoted by *Esherichia coli*RecT Protein, J. Biol. Chem., 273(20):12274-12280, (May 15, 1998).
Novy, R., et al. Ligation Independent Cloning: Efficient Directional Cloning of Pcr Products, Novagen, Inc., InNovations, 5:1-3, http://www.emdbiosciences.com/html/Nvg/inNovations.html), (1996).
Orban P.C. et al. Tissue- and site-specific Dna recombination in transgenic mice (1992) Proc. Natl. Acad. Sci. 89: 6861-6865.

(56) References Cited

OTHER PUBLICATIONS

Osawa, S., et al. Recent Evidence for Evolution of the Genetic Code, Microbiological Reviews, 56(1):229-264, (Mar. 1992).
Osborn et al., When phage, plasmids, and transposons collide: genomic islands, and conjugative and mobilizable-transposons as a mosaic continuum, Plasmid, 48:202-212, (2002).
Pachuk C.J. et al. Chain reaction cloning: one step method for directional ligation of multiple Dna fragments Gene, 243(1-2): 19-25 (2000).
Padgett et al .. Creating seamless junctions independent of restriction sites in Pcr cloning, Gene, 2 Feb. 1996, vol. 168, No. 1, pp. 31-35.
Pan et al., an approach for global scanning of single nucleotide variations, Pnas, 99(14):93469351, (Jul. 9, 2002).
Panet et al., Studies of polynucleotides: the linkage of deoxyribopolynucleotides templates to cellulose and its use in their replication. J. Biol. Chem. 249(16):5213-5221 (1974).
Parr et al., New donor vector for generation of histidine-tagged fusion proteins using the Gateway Cloning System, Plasmid, 49:179-183, (2003).
Peters et al., Tn7: Smarter Than We Thought, Nature, 2:806-814, (Nov. 2001).
Petrik et al., Advances in Transfusion Medicine in the First Decade of the 21.sup.st Century: Advances in Miniaturized Technologies, Transfusion and Apheresis Science. 45(1): 45-51 (2011).
Pon., R. Solid-phase supports for oligonucleotide synthesis, Methods Mol. Biol., 20:465-496, (1993).
Posfai, G., et al. In vivo excision and amplification of large segments of the *Escherichia coli* genome, Nucl. Acids Res., 22(12):2392-2398, (1994).
Posfai, G., et al. Markerless gene replacement in *Escherichia coli* stimulated by a double-strand break in the chromosome, Nucl. Acids Res., 27(22):4409-4415, (1999).
Prodromou et al., Recursive PCR: A Novel Technique for Total Gene Synthesis Protein Engineering, 5(8):827-829 (1992).
Ramachandran et al., End-Point Limiting-Dilution Real-Time PCR Assay for Evaluation of Hepatitis C Virus Quasispecies in Serum: Performance Under Optimal and Suboptimal Conditions, Journal of Virological Methods. 151(2): 217-224 (2008).
Ramirez et al., Engineered zinc finger nickases induce homology-directed repair with reduced mutagenic effects. Nucleic Acids Res. 2012 Jul;40(12):5560-8. doi: 10.1093/nar/gks179. Epub Feb 28. 2012.
Randegger et al., Real-time PCR and melting curve analysis for reliable and rapid detection of SHV extended-spectrum beta-lactamases. Antimicrob Agents Chemother. 2001 Jun;45(6):1730-6.
Regalado, A. Next Dream for Venter: Create Entire Set of Genes From Scratch. Wall Street Journal. Jun. 29, 2005.
Reyrat, J., et al. Counterselectable Markers: Untapped Tools for Bacterial Genetics and Pathogenesis, Infection and Immunity, 66(9):4011-4017, (Sep. 1998).
Richmond, K., et al., Amplification and assembly of chip-eluted DNA (AACED): a method for high-throughput gene synthesis, Nucleic Acids Research, 32(17): 5011-5018 (2004).
Rouillard, J. et al. Gen2Oligo: Oligonucleotide design for in vitro gene synthesis, Nucleic Acids Research, 32: W176-W180, (2004).
Rouwendal, G., et al. Enhanced Expression in Tobacco of the Gene Encoding Green Fluorescent Protein by Modification of its Codon Usage, Plant Molecular Biology, 33:989-999, (1997).
Ryu, D.D.Y., et al. Recent Progress in Biomolecular Engineering, Biotechnol. Prog. 16:2-16 (2000).
Sa-Ardyen, P., et al. The flexibility of DNA double crossover molecules, Biophys. J., 84:38293837, (Jun. 2003).
Saiki, R., et al. Analysis of enzymatically amplified beta-globin and HLA-DQ alpha DNA with allele-specific oligonucleotide probes, Nature, 324(6093):163-166, (Nov. 13, 1986).
Sakabe, N., et al. A Bioinformatics Analysis of Alternative Exon Usage in Human Genes Coding for Extracellular Matrix Proteins, Genetics and Molecular Research, 3(4):532-544, (2004).
Sakamoto, K., et al. Site-Specific Incorporation of an Unnatural Amino Acid Into Proteins in Mammalian Cells, Nucleic Acids Research, 30(21):4692-4699, (2002).
Saks, M. Making sense out of nonsense, PNAS, 98(5):2125-2127, (Feb. 27, 2001).
Saks, M., et al. An Engineered Tetrahymena tRNA.sup.Gln, for in Vivo Incorporation of Unnatural Amino Acids into Proteins by Nonsense Suppression, J. Of Biol. Chem., 271(38):23169-23175, (Sep. 20, 1996).
Salyers, A., et al. Conjugative Transposons: an Unusual and Diverse Set of Integrated Gene Transfer Elements, Microbiological Reviews, 59(4):579-590, (Dec. 1995).
Sanjana, N. et al., A Transcription activator-like effector toolbox for genome engineering, Nature Protocols, Nature Publishing Group, GB, vo. 7. No. 1, pp. 171-192, Jan. 1, 2012.
Sato et al. The cisA cistron of Bacillus subtilis sporulation gene spoIVC encodes a protein homologous to a site-specific recombinase (1990) J. Bacteriol. 172: 1092-1098.
Sato, T., et al. Production of menaquinone (vitamin K2)-7 by Bacillus subtilis, J. Of Bioscience and Engineering, 91(1):16-20, (2001).
Sauer, Functional expression of the ere-lox site-specific recombination system in the yeast Saccharomvces cerevisiae (1987) Mol. Cell. Biol. 7: 2087-2096.
Schaerli, Y., et al., ContinuoFlow polymerase Chain reaction of single-copy DNA Micorfluidic Microdroplets, Anal. Chem., 81: 302-306, (2009).
Scior, Annike et al., Directed Pcr-free engineering of highly repetitive Dna sequences, BMC Biotechnology, Biomed Central Ltd., London, GB, vol. 11, No. 1, pp. 87, Sep. 23, 2011.
Semizarov, D., et al. Stereoisomers of Deoxynucleoside 5'-Triphosphates as Substrates for Template-dependent and-independent DNA Polymerases, J. Of Biol. Chem., 272(14):9556-9560, (Apr. 4, 1997).
Seo, T., et al., Four-color DNA sequencing by synthesis on a chip using photocleavable fluorescent nucleotides, PNAS, 102(17):5926-5933, (Apr. 26, 2005).
Sgaramella, V., et al. Studies of polynucleotides, C.: A novel joining reaction catalyzed by T4-polynucleotide ligase, PNAS, 67(3):1468-1475, (Nov. 1970).
Shabarova, Z., et al., Chemical ligation of DNA: the first non-enzymatic assembly of a biologically active gene, Nucl. Acids Res., 19(15):4247-4251, (1991).
Shao, Z., et al. Random-Priming in Vitro Recombination: An Effective Tool for Directed Evolution, Nucleic Acids Research, 26(2):681-683, (1998).
Shendure et al., Accurate Multiplex Polony Sequencing of an Evolved Bacterial Genome, Science. 309:1728-1732 (2005).
Shpaer, GeneAssist. Smith-Waterman and other database similarity searches and identification of motifs: Methods Mol. Biol. 70: 173-187, 1997.
Sieber, V., et al. Libraries of Hybrid Proteins From Distantly Related Sequences, Nature Biotechnology, 19:456-460, (May 2001).
Simon, D., et al. N-methyl-D-aspartate receptor antagonists disrupt the formation of a mammalian neural map Proc Natl Acad Sci USA, 89:10593-10597, (Nov. 1992).
Smith et al., Mutation Detection with MutH, MutL, and MutS Mismatch Repair Proteins, Proc. Natl. Acad. Sci. USA, 93:4374-4379, (Apr. 1996).
Smith, H.O., et al. Generating a synthetic genome by whole genome assembly:<DX1 74 bacteriophage from synthetic oligonucleotides, PNAS, 100(26):15440-15445 (2003).
Smith, J., et al. A detailed study of the substrate specificity of a chimeric restriction enzyme. Nucleic Acids Research 27(2):674-681 (1999).
Soderlind, E., et al. Domain libraries: Synthetic diversity for de novo design of antibody V-regions, Gene, 160:269-272, (1995).
Sprinzl et al., Compilation of tRNA sequences and sequences of tRNA genes, Nucleic Acids Research, 33:D139-D140 (2005).
Stamm et al., Sanchored PCR: PCR with CDNA Coupled to a solid phase, Nucleic Acids Research, 19(6):1350, (Mar. 25, 1991).
Stekel, D., Microarrays: Making Them and Using Them, Microarray Bioinformatics. Cambridge University Press. pp. 211-230 (2003).

(56) References Cited

OTHER PUBLICATIONS

Stemmer W. P. et al., Single-step assembly of a gene and entire plasmid from large numbers of oligodeoxyribonucleotides Gene, 164 (1): 49-53, (1995).
Stemmer, DNA shuffling by random fragmentation and reassembly: in vitro recombination for molecular evolution, Proc. Natl. Acad. Sci. USA, 91:10747-10751, (1994).
Sternberg et al. Site-specific Recombination and Its Role in the Life Cycle of Bacteriophage P1 Cold Spring Harbor Symp. Quant. Biol. 45: 297-309, 1981.
Steuer, S., et al. Chimeras of the Homing Endonuclease Pi-SeeI and the Homologous Candida Tropicalis Intein: A Study to Explore the Possibility of Exchanging DNA-Binding Modules to Obtain Highly Specific Endonucleases With Altered Specificity,ChemBioChem., 5(2):206-213, (2004).
Strizhov N. et al. A synthetic cry1C gene, encoding a Bacillus thuringiensis delta-endotoxin, confers Spodoptera resistance in Alfalfa and Tobacco PNAS, 93(26):15012-15017.
Tan, S., et al. Zinc-finger protein-targeted gene regulation: Genomewide single-gene specificity, PNAS, 100(21):11997-12002, (Oct. 14, 2003).
Tang K. et al. Chip-based genotyping by mass spectrometry. PNAS, 96: 10016-10020 (1999).
Teh et al., Droplet microfluidics, Lab on Chip. 2008;8(2):198-220.
Tian, J., et al. Accurate multiplex gene synthesis from programmable DNA microchips, Nature, 432:1050-1054, (Dec. 2004).
Tsai et al., Dimeric Crispr RNA-guided FokI nucleases for highly specific genome editing. Nat Biotechnol. 2014 Jun;32(6):569-76. doi: 10.1038/nbt.2908. Epub Apr. 25, 2014 Online Methods.
Tsutakawa et al., the Structural Basis of Damaged DNA Recognition and Endonucleolytic Cleavage for Very Short Patch Repair Endonuclease, Nucleic Acids Research, 29(18):3775-3783, (2001).
Tucker et al., Massively parallel sequencing: the next big thing in genetic medicine. Am J Hum Genet. 2009 Aug;85(2):142-54. doi:10.1016/j.ajhg.2009.06.022.
Urata, H., et al. Synthesis and properties of mirror-image DNA, Nucleic Acids Research, 20(13):3325-3332 (1992).
Venkatesan et al., Improved Utility of Photolabile Solid Phase Synthesis Supports for the Synthesis of Oligonucleotides Containing 3'-Hydroxyl Termini, J. Of Org. Chem., 61:525-529, (Jan. 26, 1996).
Verma et al., Modified Oligonucleotides: Synthesis and Strategy for Users, Annu. Rev. Biochem., 67:99-134, (1998).
Vogelstein et al., Digital PCR, Pro. Natl. Acad. Sci. 96(16):9236-9241 (1999).
von Neumann, J. The general and logical theory of automata, Pergamon Press, 5:288-326, (1948).
Wang et al., De novo assembly and characterization of root transcriptome using Illumina paired-end sequencing and development of cSSR markers in sweetpotato (lpomoea batatas), BMC Genomics, 2010, vol. 11, pp. 1-14.
Wang et al., Targeted gene addition to a predetermined site in the human genome using a ZFN-based nicking enzyme. Genome Res. 2012 Jul;22(7):1316-26. doi: 10.1101/gr.122879.111. Epub Mar 20. 2012.
Waters, V. Conjugation between bacterial and mammalian cells, Nature Genetics, 29:375-376, (Dec. 2001).
Weber et al.. A Modular Cloning System for Standardized Assembly of Multigene Constructs, PLoS One, Feb. 18, 2011, vol. 6, No. 2, pp. e16765.
Weiler et al., Combining the Preparation of Oligonucleotide Arrays and Synthesis of High-Quality Primers, Analytical Biochemistry, 243:218-227, (1996).
Weisberg, et al., Site-specific recombination in Phage Lambda, in: Lambda Ii, Hendrix, et al. Eds., Cold Spring Harbor Press, Cold Spring Harbor, Ny (1983) pp. 211-250.
Werner et al., Fast track assembly of multigene constructs using Golden Gate cloning and the MoClo system, Bioengineered Bugs, Jan. 1, 2012;3(1):38-43.

Wheeler, D., et al. Database resources of the National Center for Biotechnology Information, Nucleic Acids Res., 29(1):11-16, (2001).
White et al. (Digital PCR provides sensitive and absolute calibration for high throughput sequencing, BMC Genomics, 2009, 10:116, Published: Mar. 19, 2009).
Wiedmann et al., Ligase chain reaction (LCR)—overview and applications. PCR Methods Appl. Feb. 1994; 3(4):S51-64.
Wilgenbus et al., DNA chip technology ante portas, J. Mol. Med, 77:761-768, (1999).
Xie et al., An Expanding Genetic Code, Methods A Companion to Methods in Enzymology, 36:227-238, (2005).
Xiong et al. PCR based accurate synthesis of long DNA sequences Nature protocols 1 (2): 791 (2006).
Xiong et al., Non-Polymerase-Cycling-Assembly-Based Chemical Gene Synthesis: Strategies, Methods, and Progress; Biotechnology Advances; Elsevier Publishing; Barking, GB; vol. 26; No. 2; pp. 121-134; Nov. 7, 2007.
Xiong, A., et al. A simple, rapid, high-fidelity and cost-effective PCR-based two-step DNA synthesis method for long gene sequences, Nucleic Acids Research, 32(12):e98 (10 pages), (2004).
Xu et al., A novel 5'-iodonucleoside allows efficient nonenzymatic ligation of single-stranded and duplex DNAs, Tetrahedron Letters, 38(32):5595-5598, (1997).
Xu et al., High sequence fidelity in a non-enzymatic DNA autoligation reaction, Nucleic Acids Research, 27(3):875-881, (1999).
Xu, Y., et al. Nonenzymatic autoligation in direct three-color detection of RNA and DNA point mutations, Nature Biotechnology, 19:148-152, (Feb. 2001).
Xuei et al. Use of SAM(2)(R) biotin capture membrane in microarrayed compound screening (mu ARCS) format for nucleic acid polymerization assays Journal of Biomolecular Screening 8:273282 (2003).
Yan et al., Polymer membranes with two-dimensionally arranged pores derived from monolayers of silica particles, Chem. Mater. 16(9): 1622-1626 (2004).
Yehezkel et al. (De novo DNA synthesis using single molecule PCR, Nucleic Acids Research, 2008, vol. 36, No. 17, e107, Published online Jul. 30, 2008).
Yolov et al. RNA -synthesis by use of T7-RNA-Polymerase and immobilized DNA in a flowing-type reactor. Bioorganicheskaya Khimiya, 17:789-794 (1991 ).
Yoon et al., Efficient cloning and engineering of entire mitochondrial genomes in *Escherichia coli* and transfer into transcriptionally active mitochondria, Nucleic Acids Research, 31(5):1407-1415, (2003).
Yoon, Y., et al. Cre/loxP-mediated in vivo excision of large segments from yeast genome and their amplification based on the 2 um plasmid-derived system, Gene, 223:67-76, (1998).
Young et al., Two-step Total Gene Synthesis Method Nucleic Acids Research, 32(7):e59 (6 pages), (2004).
Zha, D., et al. Assembly of Designed Oligonucleotides as an Efficient Method for Gene Recombination: A New Tool in Directed Evolution, ChemBioChem, 4:34-39, (2003).
Zhang, C., et al., PCR microfluidic devices for DNA amplification, Biotechnology Advances, 24(3):243-284, 2006.
Zhang, P. et al. Rational Design of a Chimeric Endonuclease Targeted to NotI Recognition Site Protein Engineering Design & Selection, 20(10):497-504, (Oct. 2007).
Zhang, Z., et al. Selective Incorporation of 5-Hydroxytryptophan Into Proteins in Mammalian Cells, Proceedings of the National Academy of Sciences of the United States of America, 101(24):8882-8887, (Jun. 15, 2004).
Zhao, H., et al. Molecular Evolution by Staggered Extension Process (StEP) in Vitro Recombination, Nature Biotechnology, 16:258-261, (Mar. 1998).
Zhou X. et al. Microfluidic PicoArray synthesis of oligodeoxynucleotides and simultaneous assembling of multiple DNA sequences Nucleic Acids Research , 32(18): 5409-5417 (2004).
Zhu et al., (1995). Cleavage-dependent Ligation by the FLP Recombinase. J Biol Chem 270: 23044-23054.

SEQUENCE LISTING

<160> NUMBER OF SEQ ID NOS: 1

<210> SEQ ID NO 1
<211> LENGTH: 10
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n can be a or g

<400> SEQUENCE: 1 nccaccaugg                                                                10

METHODS FOR SCREENING PROTEINS USING DNA ENCODED CHEMICAL LIBRARIES AS TEMPLATES FOR ENZYME CATALYSIS

RELATED APPLICATIONS

This is a divisional application of U.S. application Ser. No. 13/799,039, filed Mar. 13, 2013, which claims the benefit of and priority to U.S. Provisional Application No. 61/613,845, filed Mar. 21, 2012, and U.S. Provisional Application No. 61/614,213, filed Mar. 22, 2012, the disclosure of each of which is incorporated herein by reference in its entirety.

FIELD OF THE INVENTION

Methods, compositions and apparatuses provided herein relate to nucleic acid-encoded chemical libraries, and the selection of proteins with a desired enzymatic activity.

BACKGROUND

There is an increasing need to find new molecules or chemicals to effectively modulate a wide range of biological processes. There is also widespread interest in efficient synthesis and screening of large numbers of compounds to identify candidate compounds with a given desired activity. A standard way for searching for such chemicals is to screen libraries of natural or synthesized molecules.

It would thus be desirable to provide methods for preparing and screening combinatorial library of compounds.

SUMMARY

Aspects of the invention relate to methods for screening a library of proteins for a protein having a desired activity. In some embodiments, the method comprises a) providing a plurality of nucleic acids each nucleic acid having a predefined sequence at a distinct feature of a solid support; b) expressing in vitro a plurality of proteins from the plurality of nucleic acids; c) exposing each of the plurality of proteins with two single stranded oligonucleotides having complementary sequences, each oligonucleotide having a reactant and a fluorophore; d) detecting the fluorescence of the protein-reactant-oligonucleotide-fluorophore complexes; and e) isolating the complexes showing detectable fluorescence energy transfer, thereby isolating the protein having the desired enzymatic activity.

In some embodiments, in the step or providing a plurality of nucleic acids at a distinct feature of a solid support, each feature is a well of a microwell plate. In some embodiments, each nucleic acid sequences have a different nucleic acid sequence. In some embodiments, each of the plurality of proteins is expressed at a different feature of the solid support.

In some embodiments, the desired activity can comprise formation of a bond between the two reactants. In some embodiments, the protein having the desired activity specifically binds the two reactants. In some embodiments, in the step of exposing each of the plurality of protein with two oligonucleotides, the reactant is at one end of the oligonucleotide and the fluorophore is at the opposite end of the oligonucleotide. In some embodiments, the step of exposing is in the presence of a library of reactants.

In some embodiments, the method for screening a library of proteins for a protein having a desired activity comprises a) providing a plurality of nucleic acids, each nucleic acid having a predefined sequence at a distinct feature of a solid support; b) expressing in vitro a plurality of proteins from the plurality of nucleic acids; c) exposing each of the plurality of proteins with two oligonucleotides, each oligonucleotide having a reactant, wherein proteins having the desired activity bind the two reactants and form a complex with the two oligonucleotides; and d) providing a ligase, wherein the ligase catalyses the ligation of the free end of the two oligonucleotides complexed with the protein having the desired activity. In some embodiments, the two oligonucleotides are double stranded oligonucleotides. In some embodiments, two oligonucleotides are single stranded oligonucleotides and the method further comprises adding a helper oligonucleotide capable of bridging the two single stranded oligonucleotides bound to the protein having the desired activity. In some embodiments, the helper oligonucleotide is a single stranded oligonucleotide. In some embodiments, each feature is a well of a microwell plate.

In some embodiments, the method for screening a library of proteins for a protein having a desired activity comprises a) incubating a host cell comprising a first nucleic acid sequence encoding a plurality of proteins fused to aga-2 and a second nucleic acid sequence encoding a plurality of transcription activator like-effector fused with aga-1, under conditions sufficient for expressing the protein and the transcription activator like-effector as a protein complex at the cell surface; b) exposing the protein complex to a first single stranded oligonucleotide having a first reactant, wherein the oligonucleotide binds to the transcription activator like-effector; c) exposing the protein complex bound to the transcription activator like-effector, to a second single stranded oligonucleotide having a second reactant and a detectable label, wherein the second single stranded oligonucleotide has a sequence complementary to the first single stranded oligonucleotide; and d) detecting the label at the surface of the host cell, wherein the detection of the label correlates to the presence of the protein(s) having the desired activity. In some embodiments, the host cell is a yeast cell. In some embodiments, the method further comprises isolating host cells expressing the protein(s) having the desired activity.

In some embodiments, the method for screening a library of proteins for a protein having a desired activity comprises a) providing a solid surface having a plurality of anchor oligonucleotides capable of hybridizing with a plurality of double stranded nucleic acids encoding a plurality of proteins; b) hybridizing a single stranded oligonucleotide having a first reactant to a free end of the double stranded nucleic acids; c) expressing in vitro a plurality of proteins from the plurality of double stranded nucleic acids in presence of a second reactant having a detectable label; and d) identifying features having the detectable label, wherein the detection of the label correlates to a presence of the proteins having the desired activity.

DETAILED DESCRIPTION OF THE INVENTION

Figure 1:
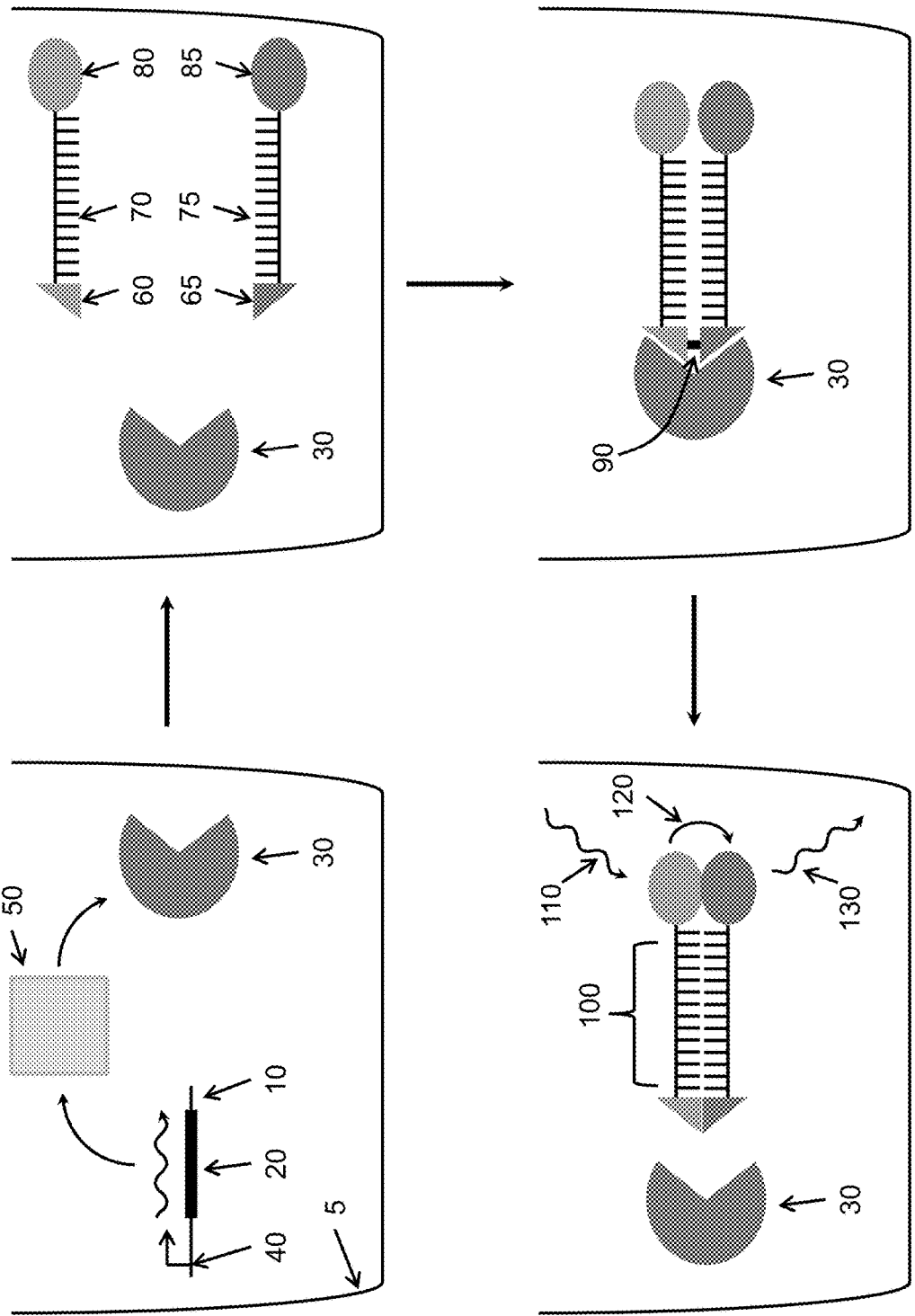
FIG. 1 illustrates a non-limiting exemplary method for screening individual synthetic nucleic acids encoding enzymes having a particular enzymatic activity.

Aspects of the invention provided herein are useful for screening proteins for desired function, such as enzymatic activities, identify candidate molecules having the desired activity or nucleic acid encoding candidate molecules having the desired activity, using nucleic acid (e.g. DNA) encoded chemical libraries.

Unless defined otherwise below, all technical and scientific terms used herein have the same meaning as commonly understood by one of ordinary skill in the art to which this disclosure belongs. Still, certain elements are defined herein for the sake of clarity. It must be noted that, as used in this specification and the appended claims, the singular forms "a", "an" and "the" include plural referents unless the context clearly dictates otherwise.

As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in the expression of the protein. When the gene encodes an untranslated RNA, it includes the promoter and the nucleic acid that encodes the untranslated RNA.

The term "gene of interest" (GOI) refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the polynucleotides that encode the protein sequences under stringent conditions, such as those described herein.

As used herein, a "polymerase" is an enzyme that catalyses synthesis of nucleic acids using a preexisting nucleic acid template. Examples include DNA polymerase (which catalyzes DNA→DNA reactions), RNA polymerase (DNA→RNA) and reverse transcriptase (RNA→DNA).

As used herein, the term "polypeptide" refers to a sequence of contiguous amino acids of any length. The terms "peptide," "oligopeptide," or "protein" may be used interchangeably herein with the term "polypeptide."

As used herein, the terms "promoter," "promoter element," or "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

As used herein, the terms "protein of interest" (POI) and "desired protein" refer to a polypeptide under study, or whose expression is desired by one practicing the methods disclosed herein. A protein of interest is encoded by its cognate gene of interest (GOI). The identity of a POI can be known or not known. A POI can be a polypeptide encoded by an open reading frame.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (UTR) of the mRNA transcript. One regulatory sequence is the ribosome binding site (RBS), which promotes efficient and accurate translation of mRNA. The prokaryotic RBS is the Shine-Dalgarno sequence, a purine-rich sequence of 5' UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence A/GCCACCAUGG (SEQ ID NO. 1), which lies within a short 5' untranslated region, directs translation of mRNA. An mRNA lacking the Kozak consensus sequence may also be translated efficiently in an in vitro system if it possesses a moderately long 5' UTR that lacks stable secondary structure. While *E. coli* ribosome preferentially recognizes the Shine-Dalgarno sequence, eukaryotic ribosomes (such as those found in retic lysate) can efficiently use either the Shine-Dalgarno or the Kozak ribosomal binding sites.

As used herein, the term "vector" refers to any genetic element, such as a plasmid, phage, transposon, cosmid, chromosome, virus, virion, etc., which is capable of replication when associated with the proper control elements and which can transfer gene sequences between cells. The vector may contain a marker suitable for use in the identification of transformed cells. For example, markers may provide tetracycline resistance or ampicillin resistance. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The term "expression vector" refers to a vector which is capable of expressing a gene that has been cloned into it. Such expression can occur after transformation into a host cell, or in IVPS systems. The cloned DNA is usually operably linked to one or more regulatory sequences, such as promoters, repressor binding sites, terminators, enhancers and the like. The promoter sequences can be constitutive, inducible and/or repressible.

As used herein, the term "host" refers to any prokaryotic or eukaryotic (e.g., mammalian, insect, yeast, plant, avian, animal, etc.) organism that is a recipient of a replicable expression vector, cloning vector or any nucleic acid molecule. The nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host," and "recombinant host cell" may be used interchangeably. For examples of such hosts, see Sambrook, et al., Molecular Cloning: A Laboratory Manual, Cold Spring Harbor Laboratory, Cold Spring Harbor, N.Y.

As used herein, "in vitro" refers to systems outside a cell or organism and may sometimes be referred to cell free system. In vivo systems relate to essentially intact cells whether in suspension or attached to or in contact with other cells or a solid. In vitro systems have an advantage of being more readily manipulated. For example, delivering components to a cell interior is not a concern; manipulations incompatible with continued cell function are also possible. However, in vitro systems can involve disrupted cells or the use of various components to provide the desired function and thus spatial relationships of the cell are lost. When an in vitro system is prepared, components, possibly critical to the desired activity can be lost with discarded cell debris. Thus in vitro systems are more manipulatable and can function differently from in vivo systems. In some embodiments, hybrid in vitro/in vivo systems can also be used.

The terms "in vitro transcription" (IVT) and "cell-free transcription" are used interchangeably herein and are intended to refer to any method for cell-free synthesis of RNA from DNA without synthesis of protein from the RNA. A preferred RNA is messenger RNA (mRNA), which encodes proteins. The terms "in vitro transcription-translation" (IVTT), "cell-free transcription-translation", "DNA template-driven in vitro protein synthesis" and "DNA template-driven cell-free protein synthesis" are used interchangeably herein and are intended to refer to any method for cell-free synthesis of mRNA from DNA (transcription) and of protein from mRNA (translation). The terms "in vitro protein synthesis" (IVPS), "in vitro translation", "cell-free translation", "RNA template-driven in vitro protein synthesis", "RNA template-driven cell-free protein synthesis" and "cell-free protein synthesis" are used interchangeably herein and are intended to refer to any method for cell-free synthesis of a protein. IVTT, including coupled transcription and transcription, is one non-limiting example of IVPS.

In some embodiments, the methods and compositions provided herein use synthetic nucleic acids. Oligonucleotides or polynucleotides of any length can be produced by the devices and methods described herein. In some embodiments, methods are provided for generating high numbers of nucleic acids such a DNA, RNA or oligonucleotides. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the terms "predetermined sequence" and "predefined sequence" is used interchangeably and means that the sequence of the polymer is known and chosen before synthesis or assembly of the polymer. In particular, aspects of the invention are described herein primarily with regard to the preparation of nucleic acids molecules, the sequence of the oligonucleotides or polynucleotides being known and chosen before the synthesis or assembly of the nucleic acid molecules. Some embodiments of the technology provided herein use immobilized oligonucleotides or polynucleotides having a predefined sequence. In some embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length.

Other terms used in the fields of recombinant nucleic acid technology and molecular and cell biology as used herein will be generally understood by one of ordinary skill in the applicable arts.

Cloning and In Vitro Expression

Some aspects of the invention provide for methods, devices and compositions for designing a protein having one or more desired characteristics, such as a desired function or property. In some embodiments, proteins can be designed and/or screened in silico. Wide varieties of computational methods and algorithms can be used to generate and/or screen libraries of proteins to identify potential proteins or protein variants that can exhibit the desired characteristic. Once a number of proteins or protein variants have been identified, nucleic acids or libraries of nucleic acids, each nucleic acid encoding each different protein or variant protein within the plurality of proteins can be synthesized. In some embodiments, the entire sequence of each nucleic acid is predetermined. The plurality of proteins or protein variants can be expressed from the plurality of nucleic acids and/or screened according to the methods disclosed herein to determine if the proteins have the desired characteristic.

In some embodiments, the invention provides arrays comprising libraries of proteins or variant proteins. In some embodiments, the library comprises at least about 100 different protein variants, with at least about 500 different protein variants being preferred, about 1000 different protein variants, about 10,000 different protein variants or more.

In some embodiments, a plurality of nucleic acids is expressed using in vitro transcription and/or translation system. In some embodiments, each nucleic acid has a predetermined sequence. Each of the plurality of nucleic acids can be generated, synthesized, assembled or deposited on a support (e.g. micro well plate or an array). The nucleic acid may be assembled by any method known in the art. The plurality of proteins, according to various embodiments, can be expressed on the same support (e.g. micro well plate or an array). Yet in other embodiments, the plurality of proteins, can be expressed on a different support. The methods described above make possible the synthesis or assembly of nucleic acids and/or proteins of any desired sequence. In some embodiments, the plurality of nucleic acids encodes nucleic acid library members. In various embodiments of the invention, the nucleic acids can be introduced into an appropriate vector by way of cloning. For example, nucleic acids can be individually cloned into an expression vector. The nucleic acid sequences may be inserted into the vector by a variety of procedures. In general, nucleic acids can be inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature.

Various vectors are publicly available. The vector may, for example, be in the form of a plasmid, cosmid, viral particle, or phage. Both expression and cloning vectors contain a nucleic acid sequence that enables the vector to replicate in one or more selected host cells. Such vector sequences are well known for a variety of bacteria, yeast, and viruses. Useful expression vectors that can be used include, for example, segments of chromosomal, non-chromosomal and synthetic DNA sequences. Suitable vectors include, but are not limited to, derivatives of SV40 and pcDNA and known bacterial plasmids such as col E1, pCR1, pBR322, pMal-C2, pET, pGEX as described by Smith, et al., Gene 57:31-40 (1988), pMB9 and derivatives thereof, plasmids such as RP4, phage DNAs such as the numerous derivatives of phage I such as NM98 9, as well as other phage DNA such as M13 and filamentous single stranded phage DNA; yeast plasmids such as the 2 micron plasmid or derivatives of the 2 m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like. The requirements are that the vectors are replicable and viable in the host cell of choice. Low- or high-copy number vectors may be used as desired.

In some embodiments, synthetic nucleic acid sequences are cloned into cloning vectors. For example, polynucleotide constructs may be introduced into an expression vector and transformed or transfected into a host cell. Any suitable vector may be used. Appropriate cloning vectors include, but are not limited to, plasmids, phages, cosmids, bacterial vector, bacterial artificial chromosomes (BACs), P1 derived artificial chromosomes (PACs), YAC, P1 vectors and the like. Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987). In some embodiments, a vector may be a vector that replicates in only one type of organism (e.g., bacterial, yeast, insect, mammalian, etc.) or in only one species of organism. Some vectors may have a broad host range. Some vectors may have different functional sequences (e.g., origins or replication, selectable markers, etc.) that are functional in different organisms. These may be used to shuttle the vector (and any nucleic acid fragment(s) that are cloned into the vector) between two different types of organism (e.g., between bacteria and mammals, yeast and mammals, etc.). In some embodiments, the type of vector that is used may be determined by the type of host cell that is chosen. Preferably, bacterium is used as a host cell and BAC vectors are utilized because of their capability to contain long nucleic acid sequences insert, typically, 50 to 350 kb (see Zhao et al., editors, Bacterial Artificial Chromosomes, Humana Press. Totowa, N.J. 2004, which is incorporated herein by reference).

In some embodiments, a library of promoter sequences is provided. In some embodiments, the library of promoters comprises a plurality of different promoters. Different promoters' sequences may be related or unrelated. In an exemplary embodiment, the promoter sequences may be obtained from a bacterial source. Each promoter sequence may be native or foreign to the polynucleotide sequence which it is operably linked to. Each promoter sequence may be any nucleic acid sequence which shows transcriptional activity in the host cell. A variety of promoters can be utilized. For example, the different promoter sequences may have different promoter strength. In some embodiments, the library of promoter sequences comprises promoter variant sequences. In some embodiments, the promoter variants can cover a wide range of promoter activities, form the weak promoter to the strong promoter. A promoter used to obtain a library of promoters may be determined by sequencing a particular host cell genome. Putative promoter sequences may be then be identified using computerized algorithms such as the Neural Network of Promoter Prediction software (Demeler et al. (Nucl. Acids. Res. 1991, 19:1593-1599). Putative promoters may also be identified by examination of family of genomes and homology analysis. The library of promoters may be placed upstream of a single gene or operon or upstream of a library of genes.

A host cell may be transformed with the resulting nucleic acid constructs using any suitable technique (e.g., electroporation, chemical transformation, infection with a viral vector, etc.). Certain host organisms are more readily transformed than others. In some embodiments, all of the nucleic acid fragments and a linearized vector are mixed together and transformed into the host cell in a single step. However, in some embodiments, several transformations may be used to introduce all the fragments and vector into the cell (e.g., several successive transformations using subsets of the fragments). It should be appreciated that the linearized vector can be designed to have incompatible ends so that it can only be circularized (and thereby confer resistance to a selectable marker) if the appropriate fragments are cloned into the vector in the designed configuration. Such design has the advantage to avoid or reduce the occurrence of "empty" vectors after selection. The nucleic acids may be introduced into the host cell by any means known in the art, including, but not limited to, transformation, transfection, electroporation, microinjection, etc. In particular non-limiting embodiments of the invention, one or more nucleic acid may be introduced into a parental host cell, which is then propagated to produce a population of progeny host cells containing the nucleic acids. Mini-prep can be performed therefrom to purify the nucleic acids for further testing (e.g., sequencing). Clones having the correct or desired nucleic acids can be subcloned for in vitro protein synthesis or in vitro transcription/translation.

The nucleic acid constructs can be constructed to include appropriate promoter and translation sequences for in vitro protein synthesis or in vitro transcription/translation. Any suitable promoter can be used, such as the ara B, tac promoter, T7, T3 or SP6 promoters amongst others. The promoter can be placed so that it is operably linked to the DNA sequences of the invention.

An In Vitro Protein Synthesis (IVPS) system, in general, includes cell extracts that support the synthesis of proteins in vitro from purified mRNA transcripts or from mRNA transcribed from DNA during the in vitro synthesis reaction. Such protein synthesis systems generally include a nucleic acid template that encodes a protein of interest. The nucleic acid template can be an RNA molecule (e.g., mRNA) or a nucleic acid that encodes an mRNA (e.g., RNA, DNA) and be in any form (e.g., linear, circular, supercoiled, single stranded, double stranded, etc.). Nucleic acid templates guide production of the desired protein. IVPS systems can also be engineered to guide the incorporation of detectably labeled amino acids, or unconventional or unnatural amino acids, into a desired protein.

In a generic IVPS reaction, a gene encoding a protein of interest (e.g. enzyme of interest) is expressed in a transcription buffer (e.g., having appropriate salts, detergents and pH), resulting in mRNA that is translated into the protein of interest in an IVPS extract and a translation buffer (e.g., having appropriate salts, detergents and pH). The transcription buffer, IVPS extract and translation buffer can be added separately, or two or more of these solutions can be combined before their addition or added contemporaneously. To synthesize a protein of interest in vitro, an IVPS extract generally at some point comprises a mRNA molecule that encodes the protein of interest. In early IVPS experiments, mRNA was added exogenously after being purified from natural sources or prepared synthetically in vitro from cloned DNA using bacteriophage RNA polymerases. In other systems, the mRNA can be produced in vitro from a template DNA; both transcription and translation occur in this type of IVPS reaction. Techniques using coupled or complementary transcription and translation systems, which carry out the synthesis of both RNA and protein in the same reaction, have been developed. In such in vitro transcription and translation (IVTT) systems, the IVPS extracts contain all the components necessary both for transcription (to produce mRNA) and for translation (to synthesize protein) in a single system. An early IVTT system was based on a bacterial extract (Lederman and Zubay, Biochim. Biophys. Acta, 149: 253, 1967). In IVTT systems, the input nucleic acid is DNA, which is normally much easier to obtain than mRNA, and more readily manipulated (e.g., by cloning, site-specific recombination, and the like).

An IVTT reaction mixture typically comprises the following components: a template nucleic acid, such as DNA, that comprises a gene of interest (GOI) operably linked to at least one promoter and, optionally, one or more other regulatory sequences (e.g., a cloning or expression vector containing the GOI); an RNA polymerase that recognizes the promoter(s) to which the GOI is operably linked and, optionally, one or more transcription factors directed to an optional regulatory sequence to which the template nucleic acid is operably linked; ribonucleotide triphosphates (rNTPs); ribosomes; transfer RNA (tRNA); optionally, other transcription factors and co-factors therefor; amino acids (optionally comprising one or more detectably labeled amino acids); one or more energy sources, (e.g., ATP, GTP); and other or optional translation factors (e.g., translation initiation, elongation and termination factors) and co-factors therefor.

In some aspects, the invention relates to high throughput expression of proteins using in vitro transcription/translation. For example, the transcription/translation reaction can take place on a solid surface or support, such as an array. In some embodiments, the transcription/translation reactions can be performed on the same support than the support for nucleic acid assembly. For example, the transcription/translation reactions can be performed at a different feature or area than the assembly reactions. Yet in another embodiment, the transcription/translation reactions can be performed on a different support.

In some embodiments, a library of synthetic nucleic acid constructs integrated into a plasmid or in linear form can be deposited into individual wells of a micro-well plate or at specific location on the support. In some embodiments, the wells can contain the appropriate transcription/translation reaction reagents. In other embodiments, the appropriate transcription/translation reaction reagents can be added to the support on which the nucleic acids have been deposited or assembled. For example, a droplet based dispensing apparatus can be used to dispense droplets of transcription/translation reagents directly onto specific locations or distinct features of the solid surface, covering the deposited nucleic acid constructs, and forming a self-contained reaction volume.

In some embodiments, the reaction reagents can be tailored to the specific type of protein being expressed. For example, prokaryotic proteins can be expressed using bacterial reagents, such as an *E. coli* lysate based expression systems, e.g., the PureExpress® system from New England Biolabs. Eukaryotic proteins can also be expressed with compatible systems, including wheat germ (e.g., T7 coupled reticulocyte lysate TNT™ system (Promega, Madison, Wis.)) and erythrocyte lysate based expression systems. Incubation of the reaction under appropriate reaction conditions, such as 37° C., can be followed by screening of protein activity.

In some embodiments, the presence of proteins of interest can be assessed by measuring protein activity. A variety of protein activities can be assayed. Non-limiting examples include binding activity (e.g., specificity, affinity, saturation, competition), enzyme activity (kinetics, substrate specificity, product, inhibition), etc. Exemplary methods include, but are not limited to, spectrophotometric, colorimetric, fluorometric, calorimetric, chemiluminescent, light scattering, radiometric, chromatographic methods.

Some aspects of the present invention relate to performing protein expression in vitro and screening of proteins for the desired characteristic, property or function. In some embodiments, libraries of proteins, for example libraries of protein variants, are expressed in vitro. In some embodiments, the nucleic acid constructs, encoding the proteins, with the appropriate regulatory sequences can be mixed with the reagents required for transcription and translation, for the on-surface production of the corresponding proteins encoded by the nucleic acids. These protein expression reactions can be performed, for example, at a micro-volume scale and in a mass parallel manner, thereby saving time and costs. These advantages make in vitro on-surface production of proteins an attractive platform for the high throughput screening of protein libraries. Methods and devices of the present invention also provide an advantageous platform for high throughput enzyme assays of in vitro produced protein libraries and in vitro development of bio-processing pathways using combinatorial protein libraries.

Some aspects of the invention relate to the screening of enzymes capable of catalyzing the formation of chemical bonds, such as covalent bonds, between two reactant molecules. In some embodiments, the proteins can be screened for their ability to catalyze carbon-carbon bond formation. For example, the methods described herein can be used to screen for enzymes capable of biocatalysing diels-alder reaction, in which a diene is bonded to a dienophile, resulting in the formation of two new C—C bonds. In other embodiments, the proteins can be screened for their ability to catalyze the addition of novel side groups on molecules, such as antibiotic molecules. In some embodiments, the methods described herein can be used for developing enzymes capable of performing novel reactions, such as the reaction of 1,3-butadiene with ethylene to produce cyclohexene. In some embodiments, the methods described herein can be used for developing enzymes capable of catalyzing carboligation reactions with a degree of control over enantiomer specificity of the final product which is not possible using classical organic chemistry.

Use of Nucleic Acid Encoded Chemical Reactants to Identify Enzymatic Activity

Some aspects of the invention relate to the screening individual synthetic genes encoding enzymes that catalyze a particular chemical reaction, such as bond formation between two reactants, e.g. reactant A and reactant B. FIG. 1 shows an exemplary process using nucleic acid (e.g. DNA) encoded libraries to screen for desired enzymatic activity. According to some embodiments, the process can be performed in individual chambers of an industry standard well plate (5). Synthetic nucleic acid constructs (10) made up of the gene of interest (GOI 20) encoding the enzyme of interest (POI 30) and the nucleic acid elements required for its expression, including promoter (40) are introduced into the wells. In certain embodiments, the nucleic acid of interest can include, in addition to the gene of interest that encodes a protein of interest, other genetic elements that regulate transcription and/or translation or facilitate selection. For example, genetic elements such as the promoter, ribosome binding site, transcriptional terminator, as well as selectable markers can be included in synthetic microarray and incorporated into the final synthetic nucleic acid construct.

Various in vitro transcription/translation systems described herein can be used. For example, for expression of eukaryotic proteins, extract of wheat germ can be used, e.g., the PureExpress® system (New England Biolabs, Ipswich, Mass.) and the T7 coupled reticulocyte lysate TNT™ system (Promega, Madison, Wis.). The in vitro expression can be performed in various formats, e.g., in a multi-well plate or on a solid surface support (e.g. array). In some embodiments, the reaction reagents can be tailored to the specific type of protein being expressed. For example, prokaryotic proteins can be expressed using bacterial reagents, such as an *E. coli* lysate based expression systems, e.g., the PureExpress® system from New England Biolabs. Eukaryotic proteins can also be expressed with compatible systems, including wheat germ (e.g., T7 coupled reticulocyte lysate TNT™ system (Promega, Madison, Wis.)) and erythrocyte lysate based expression systems.

Incubation of the synthetic nucleic acid constructs with the appropriate transcription/translation system (50) at the appropriate temperature, such as 37° C. can be followed by the screening of the activity of protein (30) encoded by the gene of interest (10).

Reactant A (60) and reactant B (65) can be individually attached to single stranded oligonucleotide strands A and B (70 and 75), respectively, each oligonucleotide having a sequence complementary to the other. A different fluorophore (80 and 85) can be attached on each oligonucleotide strand. In some embodiments, the two different fluorophores are chosen so that they can form a fluorescent energy resonance pair. For example, a first reactant (e.g. reactant A) can be attached to the 5' end and a first fluorophore can be attached the 3' end of the first oligonucleotide strand (e.g. strand A). The second reactant (e.g. reactant B) can be attached to the 3' end and the second fluorophore can be attached to the 5' end of the second oligonucleotide strand (e.g. strand B). One skilled in the art would appreciate that hybridization of the two complementary strands (strand A and strand B) can bring the two fluorophores (fluorophore A and fluorophore B) into close proximity allowing detection and quantification of the hybridization state of the two oligonucleotide strands using fluorescence resonance energy transfer (FRET). Each oligonucleotide strand can free in solution or can be anchored to a support.

In some embodiments, the synthesis of the oligonucleotide-reactant-fluorophore conjugant can be performed by adding a variety of reactive groups at each end of the oligonucleotide strand. In some embodiments, the oligonucleotide can be synthesized with the fluorescent molecule. Attachment of the reactants (A and B) can be performed by incorporating reactive groups into the other end (i.e. opposite of the fluorescent tag) of the oligonucleotide molecule. Reactive groups can include azide, amino, thiol groups, which allow for simple covalent bond formation between the oligonucleotide molecule and a reactant with an appropriate chemical group integrated into its own structure, for instance, a thiol group for formation of disulphide bonds.

In some embodiments, buffer conditions that support enzyme activity and low levels of hybridization of oligonucleotide strands A and B can be used. For example, the stringency of the hybridization can be optimized using appropriate temperature and ionic strength conditions. These factors are outlined in, for example, Sambrook et al. (Sambrook et al., Molecular Cloning: A Laboratory Manual 2nd Ed., 1989 Cold Spring Harbor Laboratory Press, Cold Spring Harbor, N.Y. which is incorporated by reference). Under appropriate conditions, duplex structure would form only if reactants A and B are stably associated, for example when the oligonucleotides can perfectly hybridize. Under perfect hybridization, the strands making up the duplex form a double stranded structure with one another and every nucleotide in each strand undergoes Watson-Crick base pairing with a nucleotide in the other strand.

One skilled in the art will appreciate that enzymes capable of catalyzing the formation of a covalent bond (90) between reactant A (60) and reactant B (65) can bring single stranded oligonucleotide strands A (70) and B (75) in close proximity with high local concentration, thereby favoring hybridization of the single stranded DNA. The hybridization of single strands A and B (100) allows for the fluorophores A and B to be into close proximity. In some embodiments, FRET can be used to detect the close proximity of the fluorophores. Incoming light (110) can be absorbed by one of the fluorophores and emitted energy can be absorbed (120) by the second fluorophore. The energy can then be emitted at a longer wavelength (130), and fluorescence is analyzed in a fluorescence spectrophotometer.

Any of a number of fluorophore combinations can be selected for use in the present invention. The fluorophores (donor) has an emission spectrum that overlaps the excitation spectrum of the other fluorophore (acceptor) and transfer of energy takes place from the donor to the acceptor through fluorescence resonance energy transfer. The energy transfer is mediated by dipole-dipole interaction. Spectroscopically, when the donor is excited, its specific emission intensity decreases while the acceptor's specific emission intensity increases, resulting in fluorescence enhancement. For efficient FRET, fluorophores attached to the single stranded oligonucleotides need to be generally 1-10 nm from each other. In some embodiments, the separations of the donor and acceptor fluorophores by about 3 to about 30 nucleotides can produce detectable fluorescence resonance energy transfer. In some embodiments, the donor fluorophore is selected that has a substantial spectrum of the acceptor fluorophore. The acceptor fluorophore has a substantial overlap of its excitation spectrum with the emission spectrum of the donor fluorophore. In addition, the wavelength maximum of the emission spectrum of the acceptor moiety is generally at least 10 nm greater than the wavelength maximum of the excitation spectrum of the donor moiety. For example, the emission spectrum of the acceptor fluorophore can be in the red portion of the visible spectrum, or in the infrared region of the spectrum.

Figure 2A:
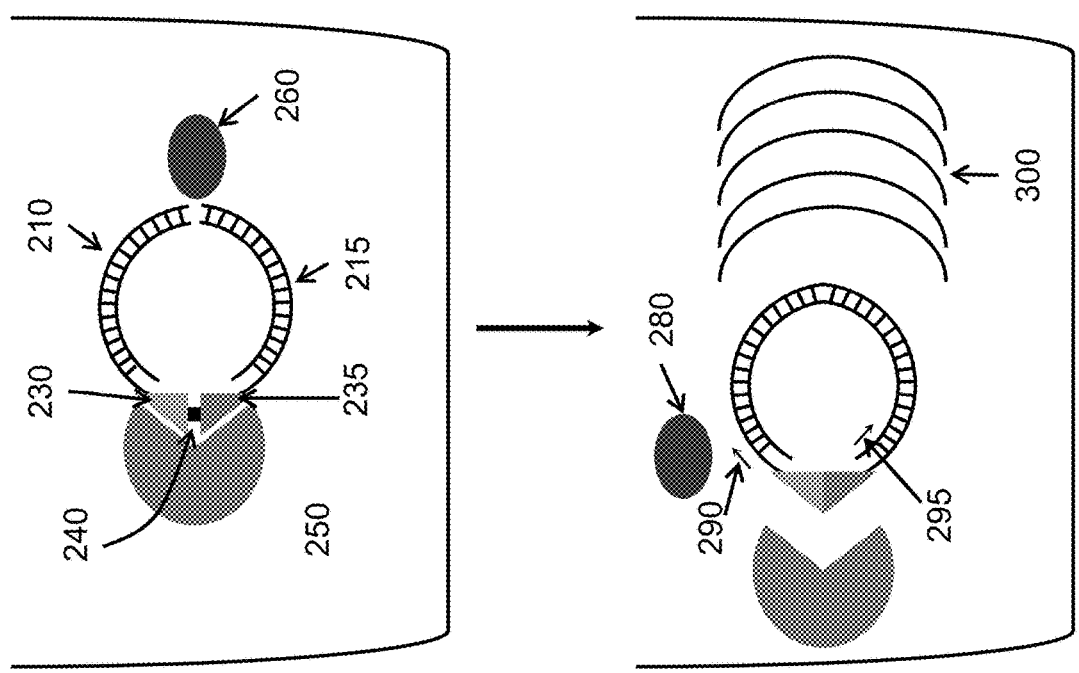
FIG. 2A illustrates a non-limiting exemplary method for screening individual synthetic nucleic acids encoding enzymes having a particular enzymatic activity.
Figure 2B:
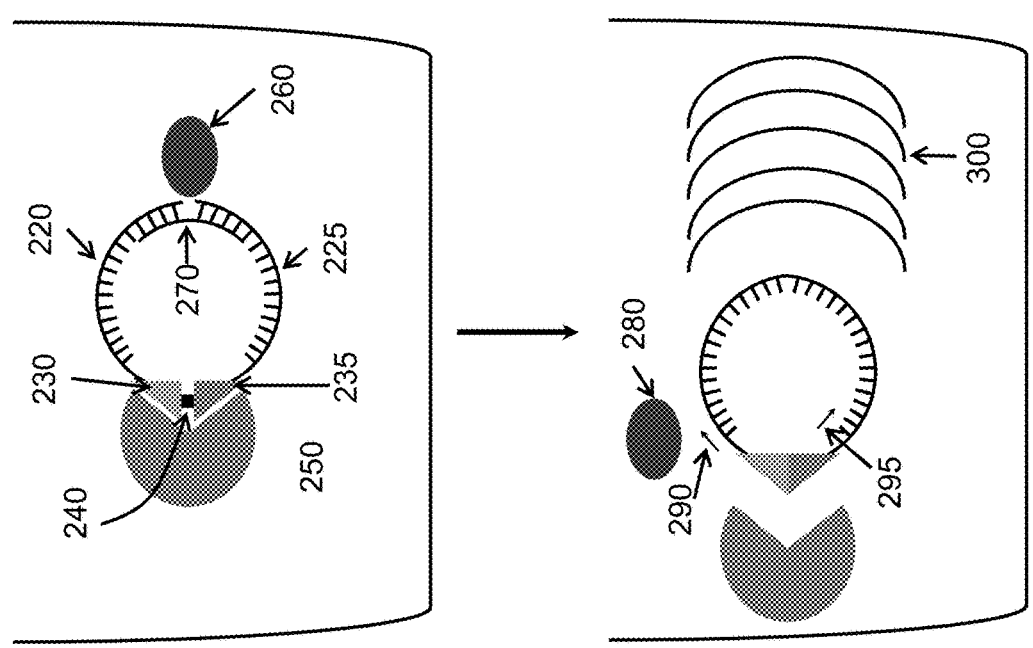
FIG. 2B illustrates a non-limiting exemplary method for screening individual synthetic nucleic acids encoding enzymes having a particular enzymatic activity using a helper oligonucleotide.

Methods for using nucleic acid encoded libraries to screen for desired enzymatic activity according to a second embodiment are depicted in FIGS. 2A and 2B. In some embodiments, double stranded nucleic acid molecule (210 and 215, FIG. 2A) or single stranded nucleic acid (220 and 225, FIG. 2B) are attached to two reactants, reactants A (230) and B (235). In some embodiments, the first reactant (e.g. reactant A) and the second reactant (reactant B) are each attached at one end (5' and 3') of the nucleic acid molecule. For example, the nucleic acid molecule is DNA. The samples can then be incubated under suitable conditions under which the bond formation (240) between the two reactants (reactants A and B) can be catalyzed by the enzyme (250). Bond formation can lead to an increased local concentration of the nucleic acid ends. In some embodiments, and referring to FIG. 2A, a ligase (260) and other necessary components can be added allowing for direct ligation of the nucleic acid ends. By ligation is meant any method of joining two or more nucleotides to each other. Ligation can include chemical or enzymatic ligation, including DNA ligase I, DNA ligase II, DNA ligase III, DNA ligase IV, E. Coli DNA ligase, T4 DNA ligase, T4 RNA ligase 1, T4 RNA ligase 2, T7 ligase, T3 DNA ligase, thermostable ligase (taq ligase) and the like.

Referring to FIG. 2B, in the case where reactants A and B are attached to a single stranded oligonucleotide, a helper oligonucleotide (270) and ligase (260) can be added. For example reactant A can be attached to the 5' end of the first single-stranded oligonucleotide and reactant B can be attached to the 3' end of the second single stranded oligonucleotide. A single stranded helper oligonucleotide can be designed to hybridize to the free end of the first and second single stranded oligonucleotides, bridging the two single stranded oligonucleotides and bringing the free end of each oligonucleotide in close proximity allowing for the ligation of the single stranded oligonucleotides.

Ligated nucleic acid strands can then be quantified using the polymerase chain reaction. In some embodiments, DNA polymerase (280), dNTPs, a pair of appropriate oligonucleotide primers (290, 295) and other necessary components can be added and the samples can be incubated under conditions appropriate to amplify ligated nucleic acid strands, thereby producing a detectable number of nucleic acid copies (300).

In some embodiments, synthetic nucleic acid constructs (10), making up of the gene of interest (20) encoding the enzyme of interest (30), and the DNA elements required for the expression of the gene of interest, including the promoter (40) are mixed in solution with reagents for in vitro transcription and translation and a labeled single stranded oligonucleotide linked to reactant A and a labeled single stranded oligonucleotide linked to reactant B. The mixture can be encapsulated into micelles. In some embodiments, FRET can be used to detect the close proximity of the fluorophores and the solution comprising the micelles can be sorted using FACS. Micelles exhibiting a detectable fluorescence at the appropriate wavelength or fluorescence energy transfer can be isolated.

Use of Nucleic Acid Encoded Chemical Reactants to Screen Enzyme Libraries

Figure 3:
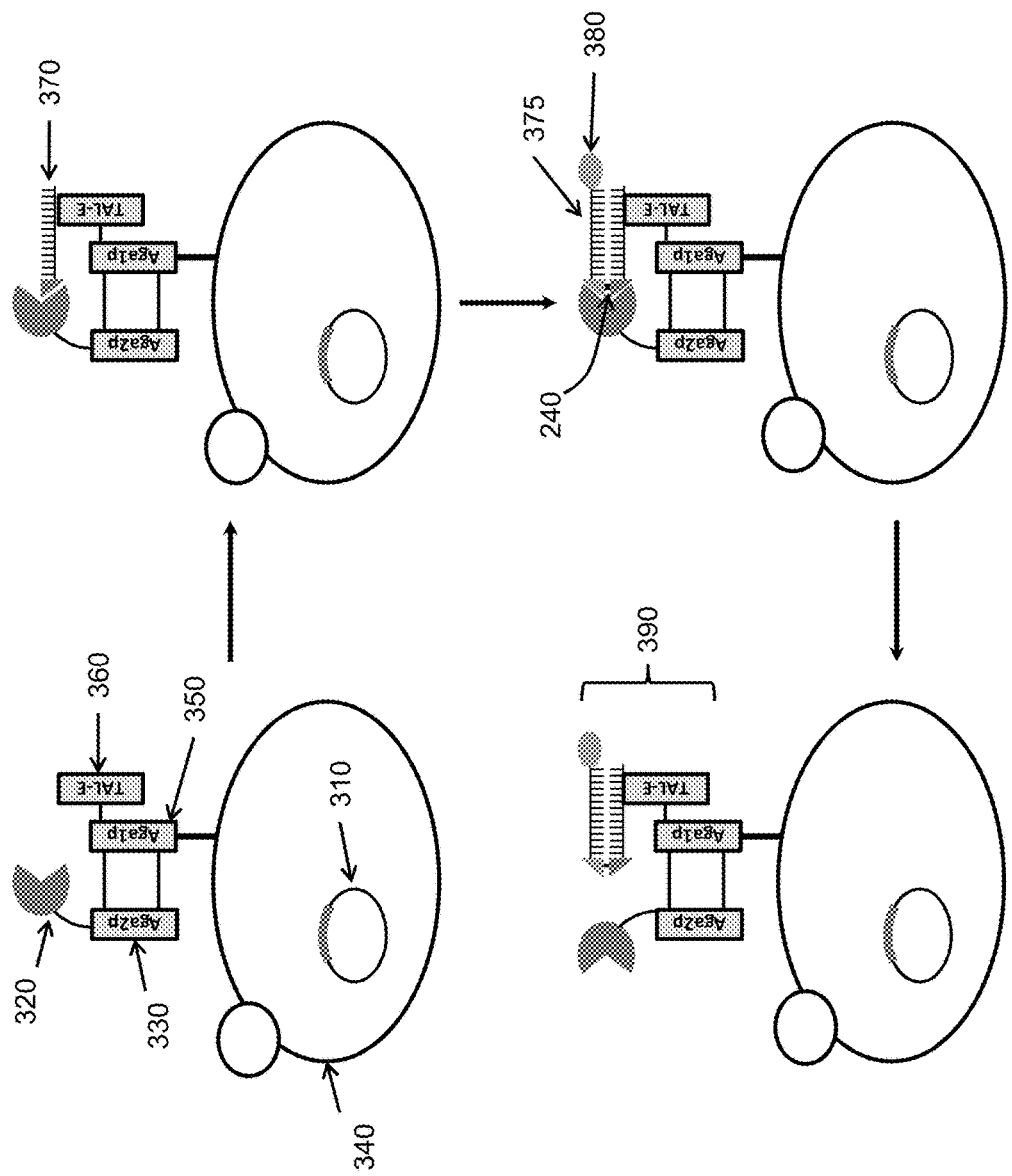
FIG. 3 illustrates a non-limiting exemplary method for screening large synthetic nucleic acids libraries encoding enzymes having a particular enzymatic activity.

Some aspects of the invention relate to the screening of large synthetic nucleic acid libraries encoding enzymes that catalyze a particular chemical reaction, such as bond formation between two reactants. FIG. 3 shows an exemplary process using such methods.

In some embodiments, and referring to FIG. 3, a library of nucleic acids encoding a library of proteins (e.g. enzymes) or proteins variants fused to Aga2p protein is synthesized. In some embodiments, the library of nucleic acids is inserted into a plasmid (310) suitable for the expression of the enzyme (320) fused with the Aga2p protein (330) in the budding yeast *Saccharomyces cerevisiae* (340). For example, proteins encoded by the nucleic acid library can be introduced on the C terminal or N-terminal region of Aga2p. Aga2p-fusion proteins can be expressed and secreted under appropriate conditions, and Aga2p-fusion proteins can be displayed on the surface of the host cell through disulfide bridges to the transmembrane protein Aga1p (350). In some embodiments, transcription activator like-effector (TAL-E) protein (360) can be fused to Aga1p and expressed the cell surface. In some embodiments, a transcription activator like-effector (TAL-E) protein (360) is expressed as a fusion with the Aga1p protein. For example, nucleic acid encoding TAL-E protein can be introduced on the C-terminal or the N-terminal of the Aga1 protein.

In some embodiments, the TAL-E fused to Aga1p can be specific for the sequence of the oligonucleotide strand attached to a first reactant (reactant A (370)). In some embodiments, TAL-E is designed to recognize specific nucleic acid sequences. TAL-Es are natural, repetitive proteins secreted by bacteria. Each of the repeats can have a set of well defined amino acid sequences that determine the nucleic acid sequence that is bound by the protein. In some embodiments, nucleic acid sequences encoding TAL-E are designed to bind specific nucleic acid sequences by modification of one or more amino acids in each of the repeats.

In some embodiments, the second reactant (reactant B (375)) attached to a single stranded oligonucleotide having a fluorescent label (380) and having a sequence complementary to the sequence of the oligonucleotide strand attached to reactant A (370) can be added. The mixture can be incubated under conditions promoting enzyme activity and hybridization of the complementary strands. Covalent bonding between the two reactants (reactant A and reactant B) by the enzyme encoded by the library results in an Aga1p bound reactant A-reactant B-fluorescent label conjugate (390). Cells can be subsequently washed to remove any unbound reactant B. In some embodiments, detection of covalent bond formation (385) between reactants A and B can be performed using fluorescent activated cell sorting (FACS) and allows for capture of cells expressing active enzymes. In some embodiments, the identity of enzymes having the desired activity (i.e. capable of catalyzing the desired reaction) can be determined by sequencing of the enzyme encoding DNA held within cells that are isolated by FACS.

Figure 4:
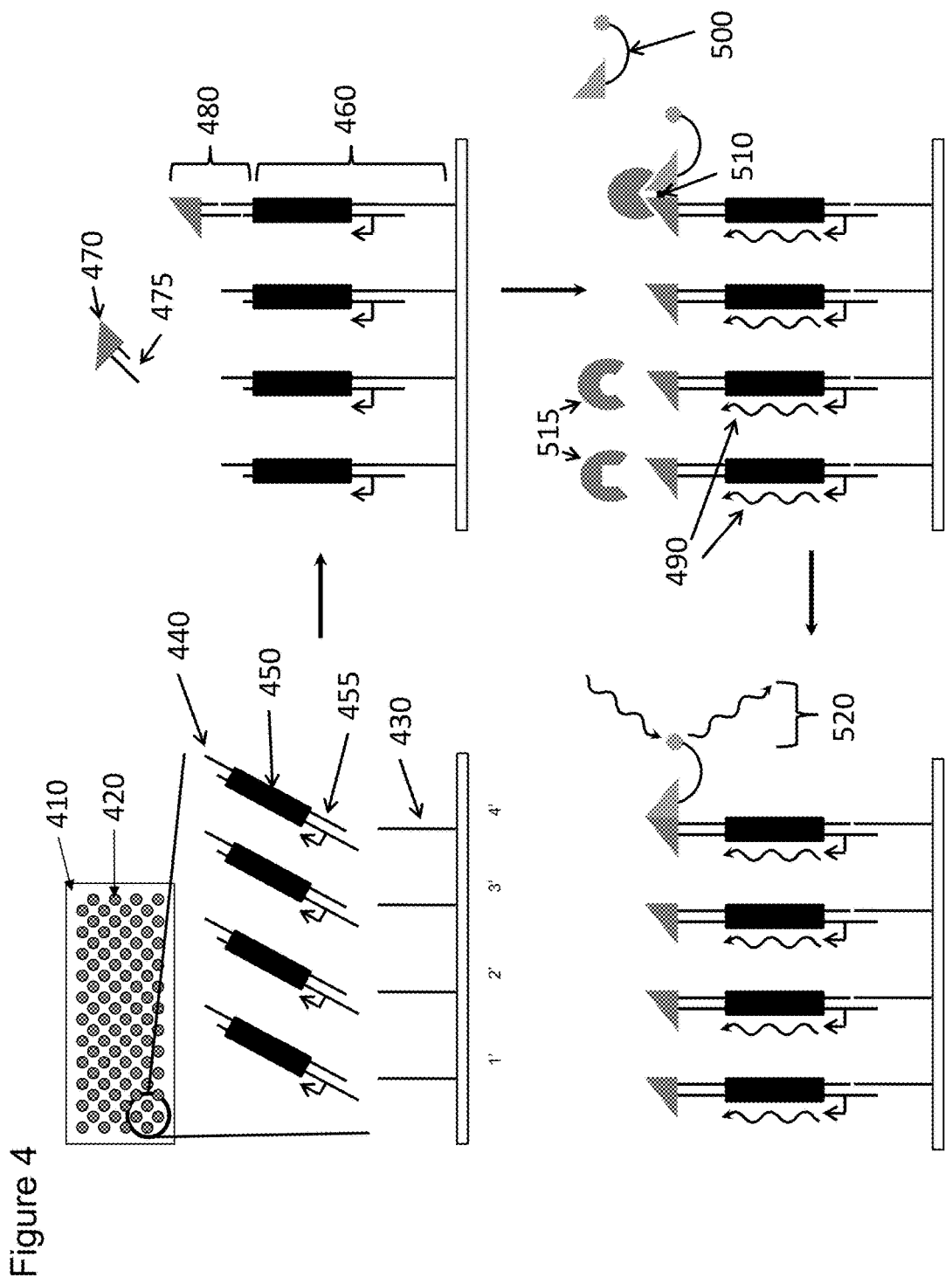
FIG. 4 illustrates a non-limiting exemplary method for screening large synthetic nucleic acids libraries encoding enzymes having a particular enzymatic activity on a solid support.

Use of Nucleic Acid Encoded Chemical Reactants to Probe Functional Protein Arrays In some aspects, the invention relates to the screening large synthetic nucleic acid libraries encoding enzymes having desired function on a solid support. In some embodiments, enzyme assays can be used to measure the activity of proteins expressed in vitro on a solid surface. In some embodiments, the solid support can be an array, such as a glass slide microarray. Referring to FIG. 4, a microarray (410) is provided. In some embodiments, each feature (420) of the microarray can comprise single stranded oligonucleotides sequences (sequences 1'-4', 430). Each oligonucleotide sequence at each specific feature allows for the specific targeting of a complementary double stranded nucleic acid sequence (440) having an extending 5' or 3' free end. In some embodiments, a library of double stranded nucleic acid sequences (440) having a sequence region complementary to the single stranded oligonucleotide sequences are immobilized through specific hybridization at specific features of the array. According to some embodiments, a synthetic nucleic acid library encoding enzymes (450) can be designed and synthesized with the genetic elements (455) required to for in vitro gene expression and a unique nucleic acid sequence to allow targeting to a specific feature of the microarray. After post-synthesis, attachment of the nucleic acid library members to the microarray (460), reactant A (470) with a covalently attached double stranded oligonucleotide (475) can be ligated to the distal, free end of the double stranded nucleic acid sequence (480).

In some embodiments, to activate the screening process, an in vitro transcription and translation mixture is added to the array. In some embodiment, the transcription/translation reaction can be generated or performed at specific features of the array. In addition to the transcription and translation mixture, fluorescently labeled reactant B (500) can be also added. After in vitro transcription and translation, enzymes (490) are produced and screened for desired function or activity. In some embodiments, enzymes having the desired activity are capable of catalyzing the covalent bond formation between the two reactants (reactants A and B (510)). The enzymes lacking the proper activity will not catalyze the bond formation (515). Bond formation between the two reactants A and B can lead to the covalent attachment of the fluorescently labeled reactant B to the nucleic acid immobilized at specific feature on the microarray. After washing away the in vitro expression mixture and unbound reactant B, the microarray can be subjected to fluorescent imaging (520) to determine microarray features having a nucleic acid sequence encoding active enzymes.

In some embodiments, the anchor or support-bound oligonucleotides are immobilized through their 3' end. It should be appreciated that by 3' end, it is meant the sequence downstream to the 5' end and by 5' end it is meant the sequence upstream to the 3' end. For example, an oligonucleotide may be immobilized on the support via a nucleotide sequence (e.g., a degenerate binding sequence), a linker or spacer (e.g., a moiety that is not involved in hybridization). In some embodiments, the anchor oligonucleotide comprises a spacer or linker to separate the anchor oligonucleotide sequence from the support. Useful spacers or linkers include photocleavable linkers, or other traditional chemical linkers. In one embodiment, oligonucleotides may be attached to a solid support through a cleavable linkage moiety. For example, the solid support may be functionalized to provide cleavable linkers for covalent attachment to the oligonucleotides. The linker moiety may be of six or more atoms in length. Alternatively, the cleavable moiety may be within an oligonucleotide and may be introduced during in situ synthesis. A broad variety of cleavable moieties are available in the art of solid phase and microarray oligonucleotide synthesis.

In some embodiments, the methods provided herein use oligonucleotides that are immobilized on a surface or substrate (e.g., support-bound oligonucleotides). As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single-stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. In some embodiments, the methods described herein use addressable oligonucleotide array formed by in situ synthesis of oligonucleotides on a solid support. In one such embodiment, at each of the multiple different addresses on the support, the in situ synthesis steps may be repeated so as to form a support comprising a plurality of oligonucleotides (e.g. same or different oligonucleotide sequences) at one or more different addresses on the support. In some embodiments, the compositions of the invention are deposited as droplets at those addresses using, for example, a pulse jet printing system. The oligonucleotides can be produced by disposing solutions on particular addressable positions in a specific order in an iterative process. In some embodiments, a device for screening libraries of nucleic acids is provided. The device can include a support having a plurality of features, each feature having a plurality of anchor oligonucleotides. In some embodiments, the plurality anchor oligonucleotides having a predefined sequence are immobilized at different discrete features of a solid support. In some embodiments, the anchor oligonucleotides are single-stranded. In some embodiments, the anchor oligonucleotides are support-bound. In some embodiments, the device comprises a solid support having a plurality of spots or features, and each of the plurality of spots includes a plurality of support-bound oligonucleotides. In some embodiments, the anchor oligonucleotides are covalently linked through their 3' end to the solid support. Yet, in other embodiments the anchor oligonucleotides are covalently linked through their 5' end to the solid support.

Figure 5:
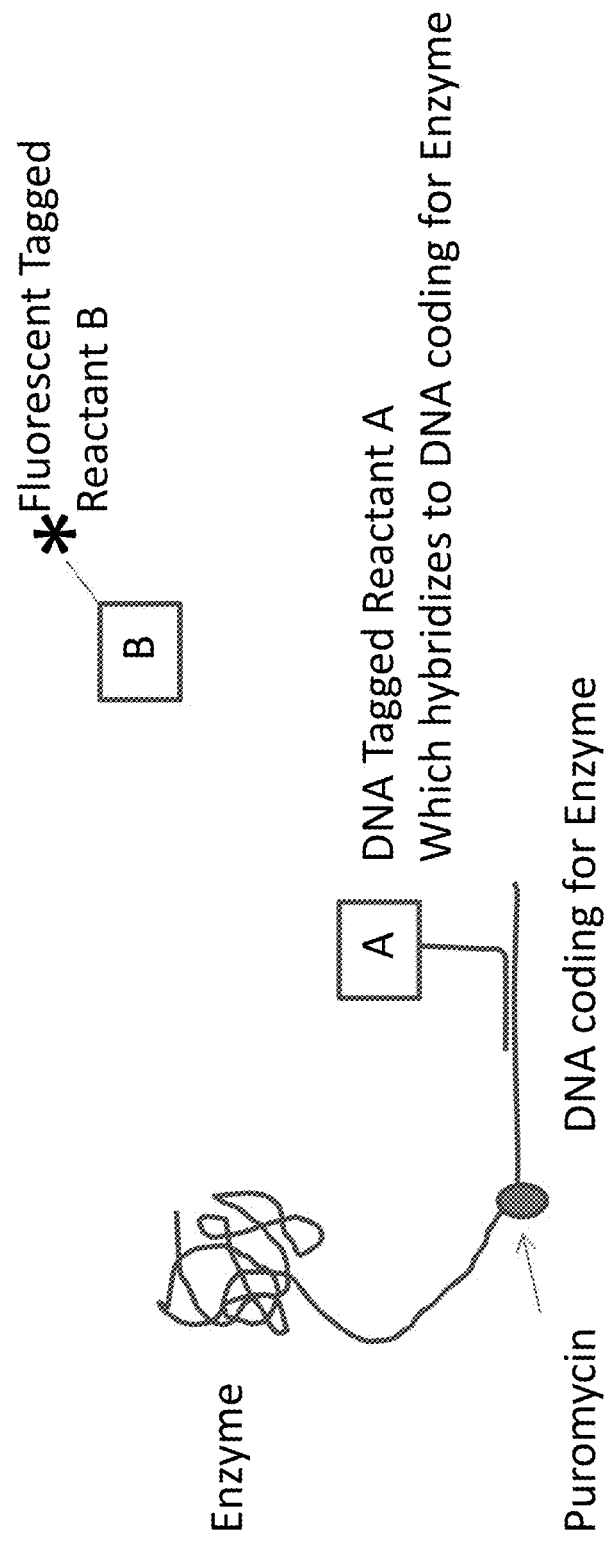
FIG. 5 illustrates a non-limiting exemplary method for screening large synthetic nucleic acids libraries encoding enzymes having a particular enzymatic activity using puromycin display.

Use of Nucleic Acid Encoded Chemical Reactants to Screen Enzyme Libraries Linked to Nucleic Acids Using the Puromycin Display System In some embodiments, puromycin display can be used to link an enzyme to the nucleic acid encoding the enzyme (see Roberts R W, Szostak J W "RNA-peptide fusions for the in vitro selection of peptides and proteins". Proc Natl Acad Sci USA. 94 (23): 12297-302). Referring to FIG. 5, Reactant A can be linked to a single stranded oligonucleotide which is complementary to the nucleic acid encoding the enzyme. Reactant B which is fluorescently labeled can be introduced. In presence of an enzyme having the desired catalytic activity, reactant B can be linked to reactant A, as described herein. The Enzyme-nucleic acid-reactant A-Reactant B complex can be detected by fluorescence and isolated. The oligonucleotide tag linked to Reactant A or nucleic acid encoding the enzyme can be sequenced to determine the enzyme having the desired activity and responsible for catalyzing the formation of the bond between reactants A and B.

Automation

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc. . . . ). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The following example is provided to further illustrate this invention and is not to be considered as unduly limiting the scope of this invention.

EXAMPLES

Condensation Reaction

Figure 6:
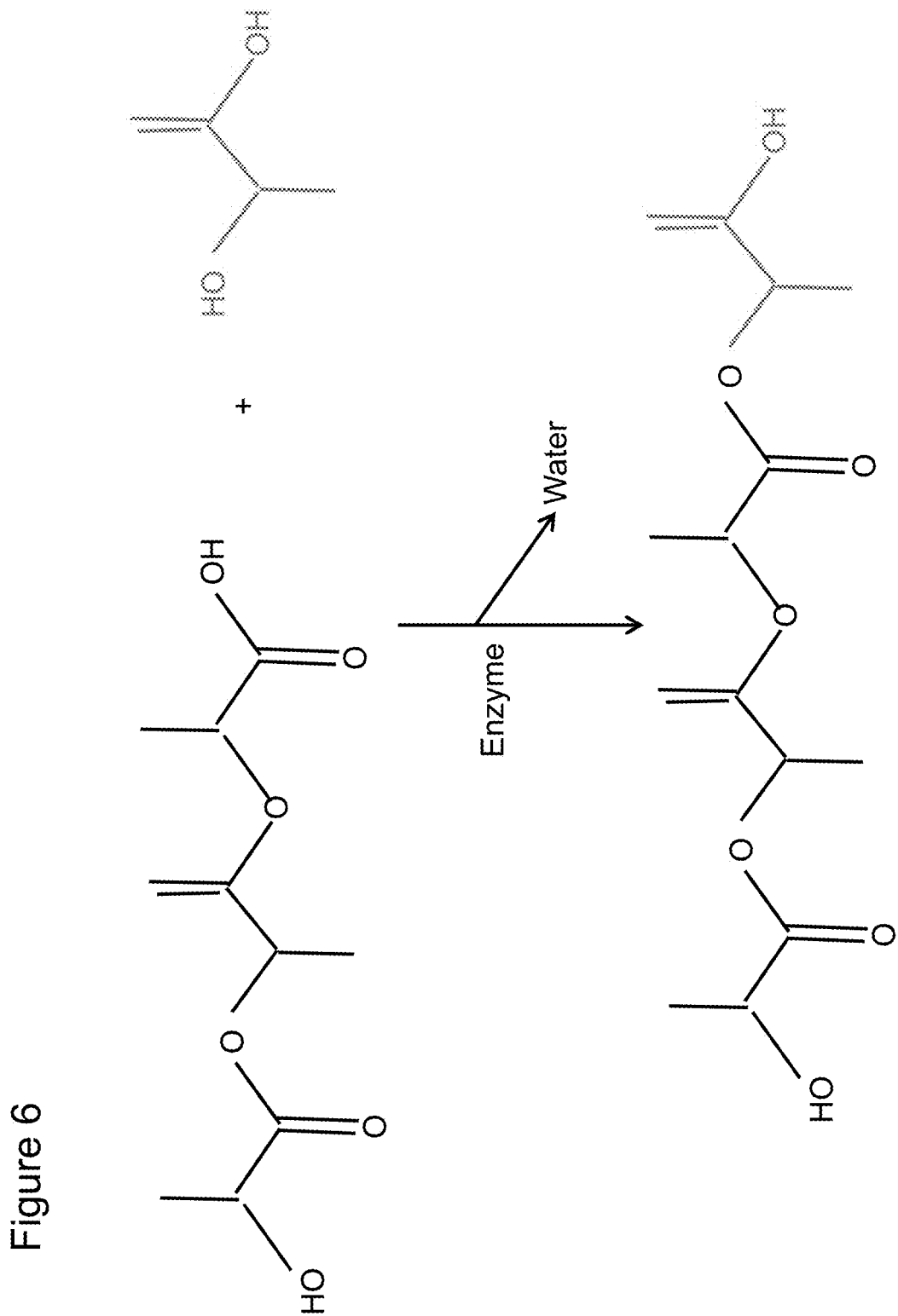
FIG. 6 illustrates a non-limiting exemplary condensation reaction using a polylactate polymerase.

FIG. 6 is a schematic drawing of a condensation reaction catalyzed by a protein having the desired catalytic activity.

In one example, the protein having the desired catalytic activity can catalyze the formation of long chain polymers, such as polyesters. In this example, a small polymerized chain of esters, such as polyetheyle terephthalate, can be uses as reactant A and an ester monomer can be used as reactant B. The process of screening described above can be used to screen for enzymes that catalyze the condensation of the ester monomer to the polyester chain. For example, libraries of proteins can be screened using the methods described herein for enzymes, such as polylactate polymerase, capable of catalyzing the synthesis of polylactic esters from monomers without passing through the standard cyclic dilactide ester chemistry.

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to U.S. provisional application 61/613, 845, filed Mar. 21, 2012 and U.S. provisional application 61/614,213, filed Mar. 22, 2012. All publications, patents and patent applications and sequence database entries mentioned herein are hereby incorporated by reference in their entirety as if each individual publication, patent or patent application is specifically and individually indicated to be incorporated by reference.

What is claimed is:

1. A method for screening a protein library for a protein having a desired activity, the method comprising:
   a) providing, at distinct features of a solid support, a plurality of nucleic acids, each nucleic acid having a predefined sequence;
   b) expressing in vitro a plurality of proteins from the plurality of nucleic acids;
   c) exposing the plurality of proteins to a first and a second oligonucleotide each, at one end, having a first and a second reactant, respectively, wherein a protein having a desired activity binds to the first and second reactants, thereby forming a complex; and
   d) ligating free ends of the first and second oligonucleotides complexed with the protein having the desired activity.

2. The method of claim 1 wherein the first and second oligonucleotides are double-stranded oligonucleotides.

3. The method of claim 1 wherein the first and second oligonucleotides are single-stranded oligonucleotides.

4. The method of claim 3 further comprising adding a helper oligonucleotide capable of bridging the single-stranded oligonucleotides bound to the protein having the desired activity.

5. The method of claim 1 wherein each distinct feature is a well of a micro well plate.

* * * * *